United States Patent
Vermeersch et al.

(10) Patent No.: US 10,000,504 B2
(45) Date of Patent: Jun. 19, 2018

(54) PSEUDOPOLYMORPHIC FORMS OF A HIV PROTEASE INHIBITOR

(71) Applicant: Janssen Sciences Ireland UC, Little Island, CO., Cork (IE)

(72) Inventors: Hans Wim Pieter Vermeersch, Ghent (BE); Daniel Joseph Christiaan Thone, Beerse (BE); Luc Donne Marie-Louise Janssens, Malle (BE); Piet Tom Bert Paul Wigerinck, Terhagen (BE)

(73) Assignee: Janssen Sciences Ireland UC, Little Island, Co. Cork (IE)

( * ) Notice: Subject to any disclaimer, the term of this patent is extended or adjusted under 35 U.S.C. 154(b) by 20 days.

(21) Appl. No.: 15/600,932

(22) Filed: May 22, 2017

(65) Prior Publication Data

US 2017/0260196 A1 Sep. 14, 2017

Related U.S. Application Data

(60) Continuation of application No. 14/817,827, filed on Aug. 4, 2015, now abandoned, which is a continuation of application No. 14/183,712, filed on Feb. 19, 2014, now abandoned, which is a continuation of application No. 13/939,494, filed on Jul. 11, 2013, now abandoned, which is a continuation of application No. 12/536,807, filed on Aug. 6, 2009, now Pat. No. 8,518,987, which is a division of application No. 10/514,352, filed as application No. PCT/EP03/50176 on May 16, 2003, now Pat. No. 7,700,645.

(30) Foreign Application Priority Data

May 16, 2002 (EP) .................................. 02076929

(51) Int. Cl.
*C07D 493/04* (2006.01)
(52) U.S. Cl.
CPC ................................. *C07D 493/04* (2013.01)
(58) Field of Classification Search
CPC ................................................... C07D 493/04
See application file for complete search history.

(56) References Cited

U.S. PATENT DOCUMENTS

| | | | |
|---|---|---|---|
| 5,413,999 | A | 5/1995 | Vacca et al. |
| 6,071,916 | A | 6/2000 | Askin et al. |
| 6,096,779 | A | 8/2000 | Chikaraishi et al. |
| 6,248,775 | B1 | 6/2001 | Vazquez et al. |
| 6,281,367 | B1 | 8/2001 | Al-Farhan et al. |
| 6,287,693 | B1 | 9/2001 | Savoir et al. |
| 7,700,645 | B2 | 4/2010 | Vermeersch et al. |
| 8,518,987 | B2 | 8/2013 | Vermeersch et al. |
| 2013/0029945 | A1 | 1/2013 | Phull et al. |
| 2015/0336980 | A1 | 11/2015 | Vermeersch |

FOREIGN PATENT DOCUMENTS

| | | |
|---|---|---|
| EP | 0715618 | 6/1996 |
| EP | 1567529 B1 | 8/2005 |
| JP | 05-230044 | 9/1993 |
| WO | WO 95/06030 A1 | 3/1995 |
| WO | WO 98/56781 | 12/1998 |
| WO | WO 99/51618 | 10/1999 |
| WO | WO 99/67254 | 12/1999 |
| WO | WO 99/67417 | 12/1999 |
| WO | WO 00/29390 | 5/2000 |
| WO | WO 00/47551 | 8/2000 |
| WO | WO 03/106461 A2 | 12/2003 |

OTHER PUBLICATIONS

"Protease inhibitors." (c) 2017. Available from: < http://www.aidsmap.com/protease-inhibitors/page/1729414/ >.*
"Civil Docket", In The United States District Court for the District of New Jersey, Case No. 2:14-cv-01370-WHW-CLW, Apr. 9, 2015, 6 pages.
"Complaint for Patent Infringement", In The United States District Court for the District of New Jersey, Case No. 2:14-cv-01370-WHW-CLW, Mar. 4, 2014, 9 pages.
"Complaint for Patent Infringement", In The United States District Court for the District of New Jersey, Case No. 2:13-cv-07576-WHW-CLW, Nov. 27, 2013, 8 pages.
"Complaint of Patent Infringement", In The United States District Court for the District of Delaware, Case No. 2:14-cv-01056-SLR, Aug. 15, 2014, 14 pages.
"Complaint of Patent Infringement", In The United States District Court for the District of New Jersey, Case No. 2:14-cv-05093-WHW-CLW, Aug. 13, 2014, 16 pages.
"Consent Judgement", In The United States District Court for the District of New Jersey, Case No. 13/7576-WHW-CLW, Mar. 26, 2014, 10 pages.
"Consolidated Guidelines on the Use of Antiretroviral Drugs for Treating and Preventing HIV Infection", World Health Organization, Jun. 2013, 271 pages.
"Crystallization", Kirh-Othmer Encyclopedia of Chemical Technology, 2002, vol. 8, 95-147.
"Darunavir", Wikipedia, https://en.wikipedia.org/wiki/Darunavir, Apr. 5, 2016, 3 pages.
"Data File of Dr. Northrup's Powder X-Ray Diffraction Testing on Compound 13", PXRD on Compound 13 Sample, Apr. 8, 2015, 1 page.
"Data File of Dr. Northrup's Powder X-Ray Diffraction Testing on Compound 13 EtOH recrystallized", PXRD on Compound 13 EtOH recrystallized Sample, Apr. 8, 2015, 1 page.

(Continued)

*Primary Examiner* — Noble E Jarrell
*Assistant Examiner* — John S Kenyon
(74) *Attorney, Agent, or Firm* — Baker & Hostetler LLP

(57) ABSTRACT

New pseudopolymorphic forms of (3R,3aS,6aR)-hexahydrofuro [2,3-b] furan-3-yl (1S,2R)-3-[[(4-aminophenyl) sulfonyl] (isobutyl) amino]-1-benzyl-2-hydroxypropylcarbamate and processes for producing them are disclosed.

19 Claims, 18 Drawing Sheets

(56) References Cited

OTHER PUBLICATIONS

"Data File of Dr. Northrup's Powder X-Ray Diffraction Testing on Compound 13 iPrOH recrystallized", PXRD on Compound 13 iPrOH recrystallized Sample, Apr. 8, 2015, 1 page.
"Data File of Dr. Northrup's Thermogravimetric Analysis sample mass testing on Compound 13", TGA on Compound 13 Sample, Apr. 8, 2015, 1 page.
"Data File of Dr. Northrup's Thermogravimetric Analysis sample mass testing on Compound 13 EtOH recrystallized", TGA on Compound 13 EtOH recrystallized Sample, Apr. 8, 2015, 1 page.
"Data File of Dr. Northrup's Thermogravimetric Analysis sample mass testing on Compound 13 iPrOH recrystallized", TGA on Compound 13 iPrOH recrystallized Sample, Apr. 8, 2015, 1 page.
"Data File of Dr. Northrup's Thermogravimetric Analysis sample Mass Spectrometry testing on Compound 13", TGA/MS on Compound 13 Sample, Apr. 8, 2015, 1 page.
"Data File of Dr. Northrup's Thermogravimetric Analysis sample Mass Spectrometry testing on Compound 13 EtOH recrystallized", TGA/MS on Compound 13 EtOH recrystallized Sample, Apr. 8, 2015, 1 page.
"Data File of Dr. Northrup's Thermogravimetric Analysis sample Mass Spectrometry testing on Compound 13 iPrOH recrystallized", TGA/MS on Compound 13 iPrOH recrystallized Sample, Apr. 8, 2015, 1 page.
"Defendants Lupin Limited's, Lupin Pharmaceuticals, Inc.'s, Mylan Pharmaceuticals Inc.'s and Mylan Inc.'s Joint Invalidity Contentions Pursuant to Local Patent Rule 3.6(b)", In the United States District Court District of New Jersey, Consolidated Civil Action No. 10-5954-WHW-MCA, Nov. 18, 2011 (Redacted), 178 pages.
"Guideline for Submitting Supporting Documentation in Drug Applications for the Manufacture of Drug Substances", Center for Drug Evaluation and Research, Feb. 1987, 20 pages.
"Hetero Drugs, Ltd.'s Certification of Non-Infringement and/or Invalidity of U.S. Pat. Nos. 5,843,946, 6,037,157, 6,248,775, 6,335,460, 6,703,403, 7,470,506, and 7,700,645", Feb. 10, 2011 (Redacted), 73 pages.
"Opinion", In The United States District Court for District of New Jersey, Case No. 2:10-cv-05954 (WHW), filed Sep. 23, 2014, 65 pages.
"Opinion", In the United States District Court for District of New Jersey, Case No. 2:10-cv-05954 (WHW), filed Sep. 23, 2014, 100 pages.
"Polymorphism in Pharmaceutical Solids", Preface, Harry G. Brittain edition, 1999, 13 pages.
"Potent HIV protease inhibitors incorporating high-affinity $P_2$-igands and (R)-(hydroxyethylamino)sulfonamide isostere", Bioorganic and Chemistry Letters, 1998, vol. 8, 687-690.
"Prescribing Information", Prezista®, Mar. 2015, 60 pages.
"Product Information", Agenerase®, Apr. 1999, 24 pages.
"Transcript of Trial Proceedings", In The United States District Court for District of New Jersey, Case No. 2:10-cv-05954 (WHW), filed Mar. 18, 2014, 35 pages.
"Waiver of the Service of Summons", In The United States District Court for the District of New Jersey, Case No. 2:14-cv-01370-WHW-CLW, Apr. 11, 2014, Document 6, 1 page.
"Waiver of the Service of Summons", In The United States District Court for the District of New Jersey, Case No. 2:14-cv-01370-WHW-CLW, Apr. 11, 2014, Document 7, 1 page.
Ahlqvist et al., "Water Dynamics in Channel Hydrates Investigated Using H/D Exchange", Intl J. of Pharmaceutics, 2002, 253-261.
Allen et al., "Systematic Analysis of Structural Data as a Research Technique in Organic Chemistry", Acc. Chem. Res., 1983, 16, 146-153.
Almarsson et al., "Crystal engineering of the composition of pharmaceutical phases. Do pharmaceutical co-crystals represent a new path to improved medicines?", Chem Commun., 2004, 1889-1896.
Ansel et al., "Pharmaceutical Dosage Forms and Drug Delivery Systems", Lippincott Williams & Wilkins, $7^{th}$ ed., 1999, 297-304.

Arrhenius, "On the Influence of Carbonic Acid in the Air Upon the Temperature of the Ground", Climate Change: Critical Concepts in the Environment, 2002, 11-44.
Aurora Analytics, "Certificate of Analysis—Compound 13 Darunavir", Apr. 8, 2015, 1 page.
Aurora Analytics, "Certificate of Analysis—Compound 13 Darunavir, ethanol recrystallized", Apr. 8, 2015, 1 page.
Aurora Analytics, "Certificate of Analysis—Compound 13 Darunavir, isopropanol recrystallized", Apr. 8, 2015, 1 page.
Aurora Analytics, "Packing Slip", Apr. 4, 2015, 1 page.
Bauer, "Ritonavir an Extraordinary Example of Conformational Polymorphism", Pharmaceutical Res., 2001, 18, 859-866.
Bernstein, "Polymorphism of Pharmaceuticals", Polymorphism in Molecular Crystals, 2002, 240-256.
Berstein, "Polymorphism in Molecular Crystals", Oxford University Press, 2002, 4-8.
Borka et al., "Crystal Polymorphism of Pharmaceuticals", Acta Pharmaceutica Jugoslavica Savez, 1990, 40, 71-94.
Braga et al., "Making Crystals from Crystals: A Green Route to Crystal Engineering and Polymorphism", Chem. Commun., 2002, 3635-3645.
Brittain et al., "Effects of Pharmaceutical Processing on Drug Polymorphs and Solvates", Polymorphism in Pharmaceutical Solids, 1999, 331-361.
Brittain, "Polymorphism in Pharmaceutical Studies", Discovery Laboratories, Inc., 1999, 205-208.
Bryn et al., "Solid-State Chemistry of Drugs", SSCI, $2^{nd}$ Edition, 1999, 12-13.
Byrn et al., "Hydrates and Solvates", Solid-State Chemistry of Drugs, $2^{nd}$ edition, 1999, 233-247.
Byrn et al., Pharmaceutical Solids a Strategic Approach to Regulatory Considerations, Pharma Res., 1995, 12(7), 945-954.
Byrn et al., "Pharmaceutical Solids: A Startegic Approach to Regulatory Considerations", 12 Pharmaceutical Res., 1995, 945-954.
Byrn et al., "Solid-State Pharmaceutical Chemistry", Chem. Mater., 1994, 6, 1148-1158.
Carlson et al., "An Integrated High Throughput Workflow for Pre-formulations: Polymorph and Salt Selection Studies", Drug Dev., 2003, 10, 6 pages.
Chemburkar et al., "Dealing with the Impact of Ritonavir Polymorphs on the Late Stages of Bulk Process Development", Org Proc Res and Dev, 2000, 4(5), 413-417.
Chikaraishi et al., "Preparation of Piretanide Polymorphs and their Physicochemical Properties and Dissolution Behaviors", Chem. Pharm. Bull., May 1994, 42(5), 1123-1128.
Chorghade, "Drug Discovery and Development, vol. 2: Drug Development", 2007, 205-208.
Cougnon et al., "Cathodic Reactivity of Platinum and Palladium in Electrolytes in Superdry Conditions", Platinum Metals Rev., 2002, 46, 94-105.
Datta et al., "Crystal structures of drugs: advances in determination, prediction, and engineering", Nature Reviews Drug Discovery, Jan. 2004, 3, 42-57.
Desiraju, "Hydration in Organic Crystals: Prediction from Molecular Structure", J. Chemical Soc'y Chemical Comm., 1991, 6, 426-428.
Docherty, "The Application of Computational Chemistry to the Study of Molecular Materials", Crystal Growth of Organic Materials, 1996, 15 pages.
English translation of European patent Application No. 02076929.5, May 16, 2002, 35 pages.
EP 1567529 & EP 2314591, Experimental Report, Jan. 29, 2013, 6 pages.
European Application No. 03753571.3: Communication to EPO, dated Jan. 29, 2013, 9 pages.
European Application No. 03753571.3: Entry into the European Phase(EPO as designated or elected office), dated Dec. 3, 2004, 5 pages.
European Patent Application No. 10180831.9: Extended European Search Report dated Feb. 28, 2011, 8 pages.
Food and Drug Administration, "Guideline for Submitting Supporting Documentation in Drug Applications for the Manufacture of

(56) References Cited

OTHER PUBLICATIONS

Drug Substances", Center for Drug Evaluation and Research, Food and Drug Administration, Department of Health and Human Services, Feb. 1987, 47 pages.
Fry, "Solvents and Supporting Electrolytes", Laboratory Techniques in Electroanalytical Chemistry, 1996, 469-485.
Gaffen et al., "Annual Cycles of Tropospheric Water Vapor", J. Geophysical Res., 1992, 97, 18185-18193.
Gao, "Physical Chemical Stability of Warfarin Sodium", AAPS PharmSci, 2001, 3(1), 1-8.
Ghosh et al., "N,N'-Disuccinimidyl Carbonate: A Useful Reagent for Alkoxycarbonylation of Amines", Tetrahedron Letters, 1992, 33, 6 pages.
Ghosh et al., "Nonpeptidal P2 Ligands for HIV Protease Inhibitors: Structure-Based Design, Synthesis, and Biological Evaluation", J. Medicinal Chemistry, 39, 1996, 15 pages.
Ghosh et al., Nonpeptidal P2 Ligands for HIV Protease Inhibitors: Structure-Based Design, Synthesis, and Biological Evaluation, J. Med. Chem., 1996, 39, 3278-3290.
Ghosh et al., "Potent HIV Protease Inhibitors Incorporating High Affinity, P2-Ligands and (R-Hydroxyethylamino) Sulfonamide Isostere", Bioorganic & Medical Chemistry Letters, Oxford, GB, Mar. 17, 1998, 8(6), 687-690.
Ghosh et al., "Potent HIV Protease Inhibitors Incorporating High-Affinity P2-Ligands and (R)-(Hydroxyethylamino)sulfonamide Isotere", 8 Bioorganic & Medicinal Chemistry Letters, 1998, 687-690.
Ghosh et al., "Potent HIV Protease Inhibitors: The Development of Tetrahydrofuranylglycines as Novel P2-Ligands and Pyrazine Amides as P3-Ligands", J. Medicinal Chemistry, 36, 1993, 14 pages.
Ghosh et al., "Structure Based Design: Novel Spirocyclic Ethers as Nonpeptidal P2-Ligands for HIV Protease Inhibitors", Bioorganic and Med. Chem. Letters 8, Feb. 1998, 687-90.
Giron et al., "Thermal Analysis and Calorimetric Methods in the Characterization of Polymorphs and Sovates", Thermochimca Acta Elsevier Science Publishers, Amsterdam, 1995, 248, 1-59.
Grant, "Theory and Origin of Polymorphism", Polymorphism in Pharmaceutical Solids 8, 1999, 19 pages.
Graziano, "Solvation thermodynamics of xenon in n-alkanes, n-alcohols and water", Biophysical Chemistry, 2003, 105, 371-382.
Grunenberg et al., "Theoretical Deviation and Practical Application of Energy Temperature Diagrams as an Instrument in Preformulation Studies of Polymorphic Drug Substances", Intl J. Pharma, 1996, 129, 147-158.
Guillory, "Generation of Polymorphs, Hydrates, Solvates, and Amorphous Solids", Polymorphism in Pharmaceutical Solids, 1999, 183-226.
Gyseghem, "Solid State Characterization of the Anti-HIV Drug TMC114: Interconversion of Amorphous TMC114, TMC114 Ethanolate and Hydrate", Eu. J. Pharm Sci. 2009, 38, 489-497.
Haleblian et al., "Pharmaceutical Applications of Polymorphism", Journal of Pharmaceutical Sciences, Aug. 1969, vol. 58, No. 8, 21 pages.
Haleblian et al., "Pharmaceutical Applications of Polymorphism", J. Pharm. Sci., Aug. 1975, 64(8), 1269-1288.
Hancock et al., "What is the True Solubility Advantage for Amorphous Pharmaceutical?", Pharmaceutical Research, 2000, 17, 397-404.
ICH Harmonized Tripartite Guideline, "Specifications: Test Procedures and Acceptance Criteria for New Drug Substances and New Drug Products: Chemical Substances, Q6A", Oct. 6, 1999, 35 pages.
In The United States Patent and Trademark Office Before the Patent Trial and Appeal Board, "Declaration of Terence L. Threlfall, Ph.D. In Support of Lupin Ltd.'s Petition for Inter Partes Review of U.S. Pat. No. 8,518,987 B2 with curriculum vitae and documents relied upon by", filed Apr. 9, 2015, 175 pages.
In The United States Patent and Trademark Office Before the Patent Trial and Appeal Board, "Declaration of Keith B. Leffler in Support of Lupin Ltd.'s Petition for Inter Partes Review of U.S. Pat. No. 8,518,987 B2 with curriculum vitae", filed Apr. 8, 2015, 30 pages.
In The United States Patent and Trademark Office Before the Patent Trial and Appeal Board, "Declaration of Frederick J. Northrup, Ph.D. In Support of Lupin Ltd.s's Petition for Inter Partes Review of U.S. Pat. No. 8,518,987 B2 with curriculum vitae", filed Apr. 9, 2015, 20 pages.
In The United States Patent and Trademark Office Before the Patent Trial and Appeal Board, "Declaration of Aristotle G. Kalivretenos, Ph.D. In Support of Lupin Ltd's Petition for Inter Partes Review of U.S. Pat. No. 8,518,987 B2 with curriculum vitae", filed Apr. 9, 2015, 40 pages.
In The United States Patent and Trademark Office Before the Patent Trial and Appeal Board, "Petition for Inter Partes Review of U.S. Pat. No. 8,518,987 B2", filed Apr. 9, 2015, 71 pages.
International Search Report re: PCT/EP03/50176, dated May 16, 2003.
Japanese Patent Application No. 513292/04: Official Action dated Sep. 1, 2009, 3 pages.
Jesley, et al., "Organic Phase Analysis, II. Two Unexpected cases of Pseudopolymorphism", Arch. Pharm. Chemi. Sci. Ed., May 1981, 9, 123-130.
Johnson et al., "Indinavir Sulfate" Analytical Profiles of Drug Substances and Excipients, Academic Press, 1999, 26, 319-357.
Jozwiakowski, Water-Insoluble Drug Formation; Chapter 15: Alteration of the Solid State of the Drug Substance: Polymorphs, Solvates, and Amorphous Forms, Interpharm Press, Jan. 5, 2001, 525-568.
Khankari et al., "Pharmaceutical Hydrates", Thermochimica Acta, 1995, 248, 61-79.
Kibbe, Handbook of Pharmaceutical Excipients, Third Edition, 2000, 18 pages.
Kirk-Othmer Encyclopedia of Chemical Technology, "Crystallization", 2002, 8, 95-147.
Lupin Ltd.'s Notification of Certification of U.S. Pat. Nos. 6,037,157; 6,703,403; 7,470,506; and 7,700,645 Pursuant to § 505(j)(2)(B)(iv) of the Federal Food, Drug, and Cosmetic Act, Jun. 3, 2011 (Redacted), 96 pages.
Lupin Pharmaceutical's, "Lupin receives Tentative Approval for Genetic PrezistaA Tablets", http://www.lupinpharmaceuticals.com/30dec2014.html, Dec. 30, 2014, 2 pages.
Lupin's Detailed Factual and Legal Basis for Lupin's Paragraph IV Certification that U.S. Pat. Nos. 6,037,157; 6,703,403; 7,470,506, and 7,700,645 are Invalid, Unenforceable, and/or Not Infringed, Oct. 1, 2010, 96 pages, Redacted.
Matsuda et al., "Physicochemical Characterization of Sprayed-Dried Phenylbutazone Polymorphs", J. Pharm. Sci, Feb. 1984, 73(2), 173-179.
McCrone, "Physics and chemistry of the Organic Solids State; Chapter 8: Polymorphism", Wiley Interscience, 1965, 2, 725-767.
Morissette et al., "High-throughput crystallization: polymorphs, salts, co-crystals and solvates of pharmaceutical solids", Advanced Drug Delivery Reviews, 2004, 56, 275-300.
Morris et al., "Hydrates", Encyclopedia of Pharmaceutical Technology, 1993, 393-440.
Morris, "Structural Aspects of Hydrates and Solvates", Polymorphism in Pharmaceutical Solids, 1999, 125-181.
Mylan's Paragraph IV Certification that U.S. Pat. Nos. 7,470,506 and 7,700,645 are Invalid, Unenforceable, and/or Not Infringed, Oct. 1, 2010, 38 pages, Redacted.
Ogata, "Operation of Chemical Experiment Procedures," K.K. Nankodo, 1963, 367-377 and 297-399.
Panel on Antiretroviral Guidelines for Adults and Adolescents, Guidelines for the Use of Antiretroviral Agents in HIV-1-Infected Adults and Adolescents, Department of Health and Human Services, Nov. 13, 2014, 282 pages.
Piekarski et al., "Dissolution enthalpy of NaI in water-alcohol mixtures at 288.15 and 308.15 K. Enthalpy of interaction in electrolyte-alcohol-water systems", Can J. Chem., 1984, 62, 856-859.
Plaintiff's Response to Invalidity Contentions of Defendants Lupin Limited, Lupin Pharmaceuticals, Inc., Mylan Pharmaceuticals Inc.,

(56) References Cited

OTHER PUBLICATIONS and Mylan Inc. Concerning U.S. Pat. No. 7,700,645 Pursuant to Local Patent Rules 3.4A and 3.6(i), Mar. 29, 2012, 62 pages.
Plaintiff's Response to Invalidity Contentions of Defendants Teva Pharmaceuticals USA, Inc. and Teva Pharmaceutical Industries, Ltd. Concerning U.S. Pat. No. 7,700,645 Pursuant to Local Patent Rules 3.4A and 3.6(i), Mar. 29, 2012, 51 pages.
Remington, "The Science and Practice of Pharmacy", Remington, $20^{th}$ edition, 2000, 649-50, 702-10, 173-77.
Salole, "The Physicochemical Properties of Oestradiol", J. Pharm. Biomed. Anal., 1987, 5(7), 635-648.
Seddon, "Pseudopolymorph: A Polemic", Crystal Growth & Design, 2004, vol. 4, No. 6, 1087.
Seddon, "Pseudopolymorph: A Polemic", Crystal Growth & Design, 2004, 4(6), 1087.
Seebach et al., "Diastereoselective a-Alkylation of β-Hydroxycarboxylic Esters Through Alkoxide Enolates: Diethyl (2S,3R)-(+)-3-Allyl-2-Hydroxysuccinate from Diethyl (s)-(-)-Malate", Organic Synthesis, 1985, 109, 11 pages.
Stahl, "The Problems of Drug Interactions with Excipients", Towards Better Safety of Drugs and Pharmaceutical Products, 1980, 265-280.
Stephenson et al., "Formation of Isomorphic Desolvates: Creating a Molecular Vacuum", J. Pharmaceutical Sci., May 1998, vol. 87, No. 5, 536-542.
Teva Pharmaceuticals USA, Inc.'s and Teva Pharmaceutical Industries, Ltd.'s Invalidity Contentions Under Local Patent Rules 3.3 and 3.6, Nov. 18, 2011 (Redacted), 123 pages.
The United States Pharmacopeia, The National Formulary, "USP 23, NF 18", 1995, 1843-1844.
Threlfall, "Analysis of Organic Polymorphs: A Review", Analyst, Oct. 1995, vol. 20, No. 10, 2435-2459.
Toth et al., "A Simple, Continuous Fluorometric Assay for HIV Protease", International Journal of Peptide & Protein Research, 1990, 36, 544-550.
U.S. Appl. No. 12/536,807: Prosecution History, Transmittal of New Application, dated Aug. 6, 2009, 6 pages.
United States Court of Appeal for the Federal Circuit, "Oral Argument Hearing Transcript", Appeal No. 2013-1360, Jun. 3, 2014, 19 pages.
U.S. Appl. No. 10/514,352: Office Action, dated Jan. 14, 2008, 10 pages.
U.S. Appl. No. 10/514,352: Office Action, dated Nov. 3, 2008, 9 pages.
U.S. Appl. No. 10/514,352: Response and Amendment, dated Jul. 14, 2008, 7 pages.
U.S. Appl. No. 10/514,352: Transmittal Letter to the United States Designated/Elected Office (DO/EO/US) Concerning a Filing Under 35 U.S.C. 371, dated Nov. 12, 2004, 3 pages.
U.S. Appl. No. 12/536,807: Appellant's Brief Pursuant to 37 CFR § 41.37, dated Jan. 25, 2013, 12 pages.
U.S. Appl. No. 12/536,807: Final Rejection, dated May 22, 2012, 9 pages.
U.S. Appl. No. 12/536,807: Non-Final Office Action, dated Sep. 12, 2011, 9 pages.
U.S. Appl. No. 12/536,807: Notice of Panel Decision from pre-Appeal Brief Review, dated Oct. 25, 2012, 2 pages.
U.S. Appl. No. 12/536,807: Pre-Appeal Brief Request for Review, dated Sep. 17, 2012, 5 pages.
U.S. Appl. No. 12/536,807: Reply pursuant to 37 CFR § 1.111, dated Mar. 12 2012, 8 pages.
U.S. Appl. No. 12/536,807: Reply pursuant to 37 CFR § 1.116, dated Jul. 20, 2012, 10 pages.
U.S. Appl. No. 12/536,807: Supplemental Preliminary Amendment, dated Jul. 2, 2010, 5 pages.
Van Gyseghem et al., "Solid State Characterization of the Anti-HIV Drug TMC114: Interconvertsion of Amorphous TMC114 Ethanolate and Hydrate", Eur. J. Pharmaceutical Sci., 2009, 38, 489-497.
Vermeersch et al., "Pseudopolymorphic Forms of a HIV Protease Inhibitor", Tibotec Pharma, Caplus No. 1006987, 140:47540, 2003, 1 page.
Vippagunta et al., "Crystalline Solids", Advanced Drug Delivery Reviews, 2001, 48, 3-26.
Zumdahl, "Chemisrty", D.C. Heath and Company, 1986, 31-59, 295-347, 383-433, and 559-613.

\* cited by examiner

PSEUDOPOLYMORPHIC FORMS OF A HIV PROTEASE INHIBITOR

CROSS REFERENCE TO RELATED APPLICATIONS

This application is a continuation of U.S. application Ser. No. 14/817,827, filed Aug. 4, 2015, which is a continuation of U.S. application Ser. No. 14/183,712, filed Feb. 19, 2014, now abandoned, which is a continuation of U.S. application Ser. No. 13/939,494, filed Jul. 11, 2013, now abandoned, which is a continuation of U.S. Pat. No. 8,518,987, filed Aug. 6, 2009, which is a division of U.S. Pat. No. 7,700,645, filed Nov. 12, 2004, which is the national stage of International Application No. PCT/EP2003/50176, filed May 16, 2003, which claims the benefit of European Patent Application No. 02076929.5, filed May 16, 2002, the disclosures of which are incorporated herein in their entireties.

TECHNICAL FIELD

This invention relates to novel pseudopolymorphic forms of (3R,3aS,6aR)-hexahydrofuro [2,3-b] furan-3-yl (1S,2R)-3-[[(4-aminophenyl) sulfonyl] (isobutyl) amino]-1-benzyl-2-hydroxypropylcarbamate, a method for their preparation as well as their use as a medicament.

BACKGROUND OF THE INVENTION

Virus-encoded proteases, which are essential for viral replication, are required for the processing of viral protein precursors. Interference with the processing of protein precursors inhibits the formation of infectious virions. Accordingly, inhibitors of viral proteases may be used to prevent or treat chronic and acute viral infections. (3R,3aS,6aR)-hexahydrofuro [2,3-b] furan-3-yl (1S,2R)-3-[[(4-aminophenyl) sulfonyl] (isobutyl) amino]-1-benzyl-2-hydroxypropylcarbamate has HIV protease inhibitory activity and is particularly well suited for inhibiting HIV-1 and HIV-2 viruses.

The structure of (3R,3aS,6aR)-hexahydrofuro [2,3-b] furan-3-yl (1S,2R)-3-[[(4-amino-phenyl) sulfonyl] (isobutyl) amino]-1-benzyl-2-hydroxypropylcarbamate, is shown below:

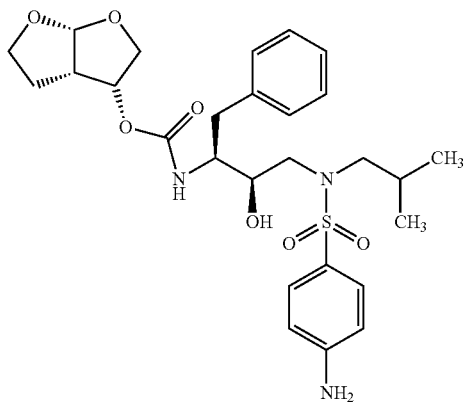

Formula (X)

Compound of formula (X) and processes for its preparation are disclosed in EP 715618, WO 99/67417, U.S. Pat. No. 6,248,775, and in *Bioorganic and Chemistry Letters*, Vol. 8, pp. 687-690, 1998, "Potent HIV protease inhibitors incorporating high-affinity $P_2$-igands and (R)-(hydroxyethylamino)sulfonamide isostere", all of which are incorporated herein by reference.

Drugs utilized in the preparation of pharmaceutical formulations for commercial use must meet certain standards, including GMP (Good Manufacturing Practices) and ICH (International Conference on Harmonization) guidelines. Such standards include technical requirements that encompass a heterogeneous and wide range of physical, chemical and pharmaceutical parameters. It is this variety of parameters to consider, which make pharmaceutical formulations a complex technical discipline.

For instance, and as example, a drug utilized for the preparation of pharmaceutical formulations should meet an acceptable purity. There are established guidelines that define the limits and qualification of impurities in new drug substances produced by chemical synthesis, i.e. actual and potential impurities most likely to arise during the synthesis, purification, and storage of the new drug substance. Guidelines are instituted for the amount of allowed degradation products of the drug substance, or reaction products of the drug substance with an excipient and/or immediate container/closure system.

Stability is also a parameter considered in creating pharmaceutical formulations. A good stability will ensure that the desired chemical integrity of drug substances is maintained during the shelf-life of the pharmaceutical formulation, which is the time frame over which a product can be relied upon to retain its quality characteristics when stored under expected or directed storage conditions. During this period the drug may be administered with little or no risk, as the presence of potentially dangerous degradation products does not pose prejudicial consequences to the health of the receiver, nor the lower content of the active ingredient could cause under-medication.

Different factors, such as light radiation, temperature, oxygen, humidity, pH sensitivity in solutions, may influence stability and may determine shelf-life and storage conditions.

Bioavailability is also a parameter to consider in drug delivery design of pharmaceutically acceptable formulations. Bioavailability is concerned with the quantity and rate at which the intact form of a particular drug appears in the systemic circulation following administration of the drug. The bioavailability exhibited by a drug is thus of relevance in determining whether a therapeutically effective concentration is achieved at the site(s) of action of the drug.

Physico-chemical factors and the pharmaco-technical formulation can have repercussions in the bioavailability of the drug. As such, several properties of the drug such as dissociation constant, dissolution rate, solubility, polymorphic form, particle size, are to be considered when improving the bioavailability.

It is also relevant to establish that the selected pharmaceutical formulation is capable of manufacture, more suitably, of large-scale manufacture.

In view of the various and many technical requirements, and its influencing parameters, it is not obvious to foresee which pharmaceutical formulations will be acceptable. As such, it was unexpectedly found that certain modifications of the solid state of compound of formula (X) positively influenced its applicability in pharmaceutical formulations.

SUMMARY OF THE INVENTION

Present invention concerns pseudopolymorphic forms of compound of formula (X) for the preparation of pharmaceutical formulations. Such pseudopolymorphic forms contribute to pharmaceutical formulations in improved stability and bioavailability. They can be manufactured in sufficient high purity to be acceptable for pharmaceutical use, more particularly in the manufacture of a medicament for inhibiting HIV protease activity in mammals.

In a first aspect, the present invention provides pseudopolymorphs of (3R,3aS,6aR)-hexahydrofuro [2,3-b] furan-3-yl (1S,2R)-3-[[(4-aminophenyl) sulfonyl] (isobutyl) amino]-1-benzyl-2-hydroxypropylcarbamate.

Pseudopolymorphs provided include alcohol solvates, more in particular, C1-C4 alcohol solvates; hydrate solvates; alkane solvates, more in particular, C1-C4 chloroalkane solvates; ketone solvates, more in particular, C1-C5 ketone solvates; ether solvates, more in particular, C1-C4 ether solvates; cycloether solvates; ester solvates, more in particular, C1-C5 ester solvates; and sulfonic solvates, more in particular, C1-4 sulfonic solvates, of the compound of formula (X). Preferred pseudopolymorphs are pharmaceutically acceptable solvates, such as hydrate and ethanolate.

Particular pseudopolymorphs are Form A (ethanolate), Form B (hydrate), Form C (methanolate), Form D (acetonate), Form E (dichloromethanate), Form F (ethylacetate solvate), Form G (1-methoxy-2-propanolate), Form H (anisolate), Form I (tetrahydrofuranate), Form J (isopropanolate) of compound of formula (X). Another particular pseudopolymorph is Form K (mesylate) of compound of formula (X).

In a second aspect, present invention relates to processes for preparing pseudopolymorphs. Pseudopolymorphs of compound of formula (X) are prepared by combining compound of formula (X) with an organic solvent, water, or mixtures of water and water miscible organic solvents, and applying any suitable technique to induce crystallization, to obtain the desired pseudopolymorphs.

In a third aspect, the invention relates to the use of the present pseudopolymorphs, in the manufacture of pharmaceutical formulations for inhibiting HIV protease activity in mammals. In relation to the therapeutic field, a preferred embodiment of this invention relates to the use of pharmaceutically acceptable pseudopolymorphic forms of compound of formula (X) for the treatment of an HIV viral disease in a mammal in need thereof, which method comprises administering to said mammal an effective amount of a pharmaceutically acceptable pseudopolymorphic form of compound of formula (X).

The following drawings provide additional information on the characteristics of the pseudopolymorphs according to present invention.

BRIEF DESCRIPTION OF THE DRAWINGS

In FIGS. 5, 6, and 7, P1 corresponds to Form A, P18 corresponds to Form B, P19 corresponds to amorphous form, P25 corresponds to Form E, P27 corresponds to Form F, P50 corresponds to Form D, P68 corresponds to Form H, P69 corresponds to Form C, P72 corresponds to Form I, and P81 corresponds to Form G.

DETAILED DESCRIPTION

Figure 1:
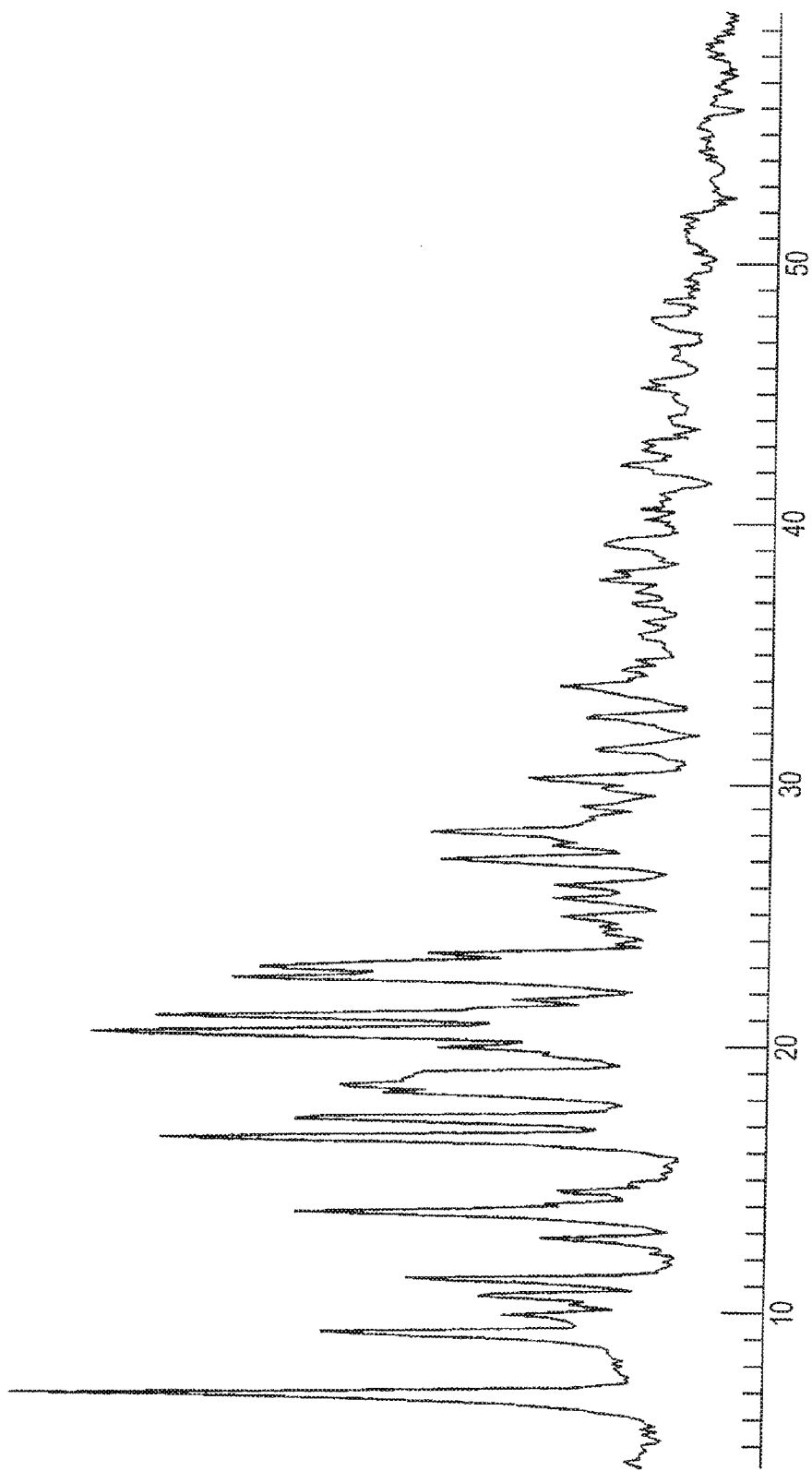
FIG. 1, FIG. 2 and FIG. 3 are the powder X-ray diffraction patterns of the Form A (1:1).

The term "polymorphism" refers to the capacity of a chemical structure to occur in different forms and is known to occur in many organic compounds including drugs. As such, "polymorphic forms" or "polymorphs" include drug substances that appear in amorphous form, in crystalline form, in anhydrous form, at various degrees of hydration or solvation, with entrapped solvent molecules, as well as substances varying in crystal hardness, shape and size. The different polymorphs vary in physical properties such as solubility, dissolution, solid-state stability as well as processing behaviour in terms of powder flow and compaction during tabletting.

The term "amorphous form" is defined as a form in which a three-dimensional long-range order does not exist. In the amorphous form the position of the molecules relative to one another are essentially random, i.e. without regular arrangement of the molecules on a lattice structure.

The term "crystalline" is defined as a form in which the position of the molecules relative to one another is organised according to a three-dimensional lattice structure.

The term "anhydrous form" refers to a particular form essentially free of water. "Hydration" refers to the process of adding water molecules to a substance that occurs in a particular form and "hydrates" are substances that are formed by adding water molecules. "Solvating" refers to the process of incorporating molecules of a solvent into a substance occurring in a crystalline form. Therefore, the term "solvate" is defined as a crystal form that contains either stoichiometric or non-stoichiometric amounts of solvent. Since water is a solvent, solvates also include hydrates. The term "pseudopolymorph" is applied to polymorphic crystalline forms that have solvent molecules incorporated in their lattice structures. The term pseudopolymorphism is used frequently to designate solvates (Byrn, Pfeiffer, Stowell, (1999) *Solid-state Chemistry of Drugs,* 2nd Ed., published by SSCI, Inc).

The present invention provides pseudopolymorphs of (3R,3aS,6aR)-hexahydrofuro [2,3-b] furan-3-yl (1S,2R)-3-[[(4-aminophenyl) sulfonyl] (isobutyl) amino]-1-benzyl-2-hydroxypropylcarbamate.

In one embodiment pseudopolymorphs are alcohol solvates, more in particular, $C_1$-$C_4$ alcohol solvates; hydrate solvates; alkane solvates, more in particular, $C_1$-$C_4$ chloroalkane solvates; ketone solvates, more in particular, $C_1$-$C_5$ ketone solvates; ether solvates, more in particular $C_1$-$C_4$ ether solvates; cycloether solvates; ester solvates, more in particular $C_1$-$C_5$ ester solvates; or sulfonic solvates, more in particular, $C_1$-$C_4$ sulfonic solvates, of the compound of formula (X). The term "$C_1$-$C_4$ alcohol" defines straight and/or branched chained saturated and unsaturated hydrocarbons having from 1 to 4 carbon atoms substituted with at least a hydroxyl group, and optionally substituted with an alkyloxy group, such as, for example, methanol, ethanol, isopropanol, butanol, 1-methoxy-2-propanol and the like. The term "$C_1$-$C_4$ chloroalkane" defines straight and/or branched chained saturated and unsaturated hydrocarbons having from 1 to 4 carbon atoms substituted with at least one chloro atom, such as, for example, dichloromethane. The term "$C_1$-$C_5$ ketone" defines solvents of the general formula R'—C(=O)—R wherein R and R' can be the same or different and are methyl or ethyl, such as, acetone and the like. The term "$C_1$-$C_4$ ether" defines solvents of the general formula R'—O—R wherein R and R' can be the same or different and are a phenyl group, methyl or ethyl, such as, anisole and the like. The term "cycloether" defines a 4- to 6-membered monocyclic hydrocarbons containing one or two oxygen ring atoms, such as tetrahydrofuran and the like. The term "$C_1$-$C_5$ ester" defines solvents of the general formula R'—O—C(=O)—R wherein R and R' can be the same or different and are methyl or ethyl, such as ethylacetate and the like. The term "$C_1$-$C_4$ sulfonic solvent" defines solvents of the general formula R—$SO_3$H wherein R can be a straight or branched chained saturated hydrocarbon having from 1 to 4 carbon atoms, such as mesylate, ethanesulfonate, butanesulfonate, 2-methyl-1-propanesulfonate, and the like.

Pseudopolymorphs of the present invention, which are pharmaceutically acceptable, for instance hydrates, alcohol solvates, such as, ethanolate, are preferred forms.

Several pseudopolymorphs are exemplified in this application and include Form A (ethanolate), Form B (hydrate), Form C (methanolate), Form D (acetonate), Form E (dichloromethanate), Form F (ethylacetate solvate), Form G (1-methoxy-2-propanolate), Form H (anisolate), Form I (tetrahydrofuranate), Form J (isopropanolate), or Form K (mesylate) of compound of formula (X).

Solvates can occur in different ratios of solvation. Solvent content of the crystal may vary in different ratios depending on the conditions applied. Solvate crystal forms of compound of formula (X) may comprise up to 5 molecules of solvent per molecule of compound of formula (X), appearing in different solvated states including, amongst others, hemisolvate, monosolvate, disolvate, trisolvate crystals, intermediate solvates crystals, and mixtures thereof. Conveniently, the ratio of compound of formula (X) to the solvent may range between (5:1) and (1:5). In particular, the ratio may range from about 0.2 to about 3 molecules of solvent per 1 molecule of compound of formula (X), more in particular, the ratio may range from about 1 to about 2 molecules of solvent per 1 molecule of compound of formula (X), preferably the ratio is 1 molecule of solvent per 1 molecule of compound of formula (X).

Solvates may also occur at different levels of hydration. As such, solvate crystal forms of compound of formula (X) may in addition comprise under certain circumstances, water molecules partially or fully in the crystal structures. Consequently, the term "Form A" will be used herein to refer to the ethanolate forms of compound of formula (X) comprising up to 5 molecules of solvent per 1 molecule of compound of formula (X), intermediate solvates crystals, and the mixtures thereof; and optionally comprising additional water molecules, partially or fully in the crystal structures. The same applies for Form B through Form K. In case a particular "Form A" needs to be denoted, the ratio of solvation will follow the "Form A", for instance, one molecule of ethanol per one molecule of compound (X) is denoted as Form A (1:1).

Figure 2:
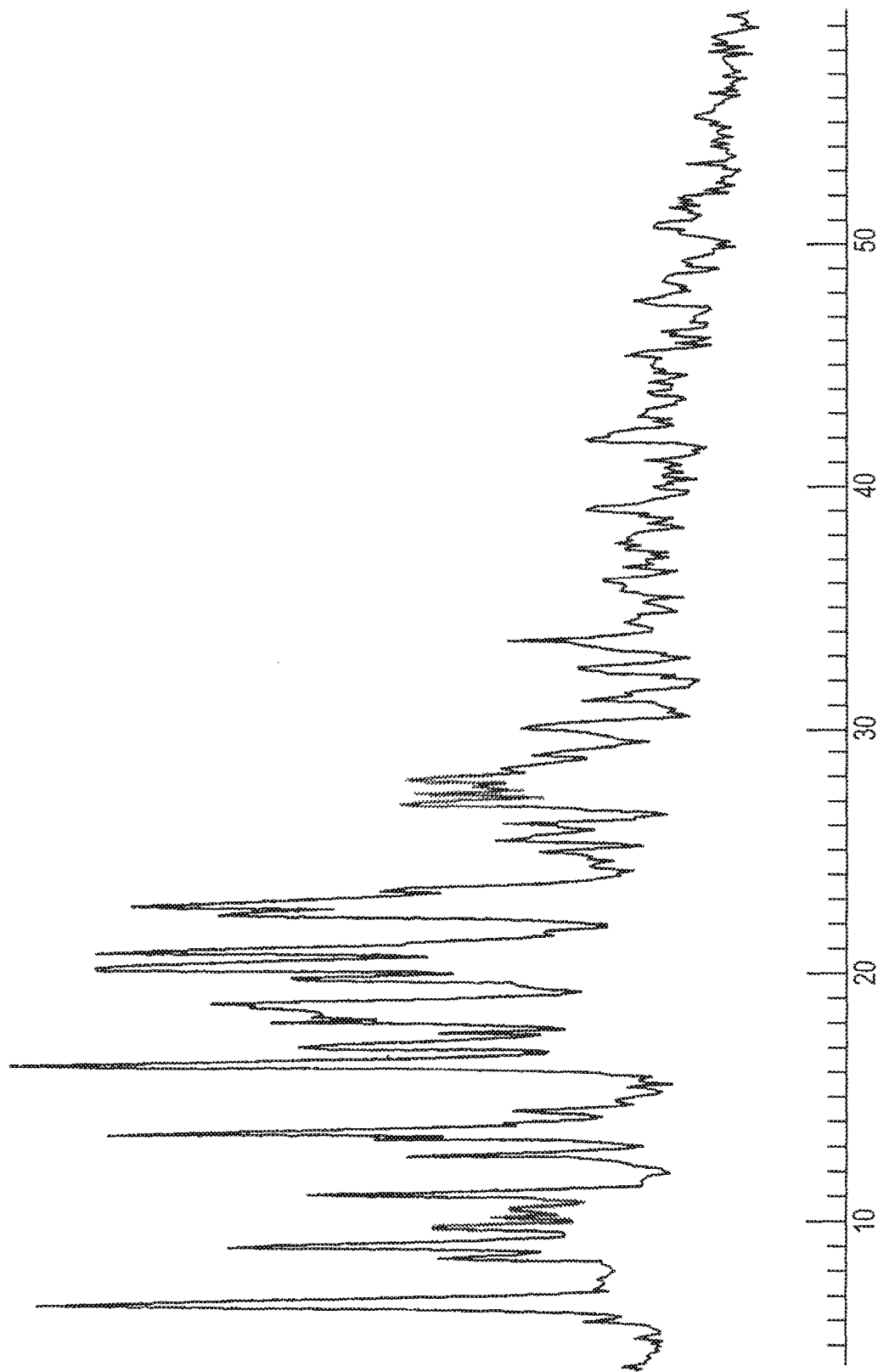
Figure 3:
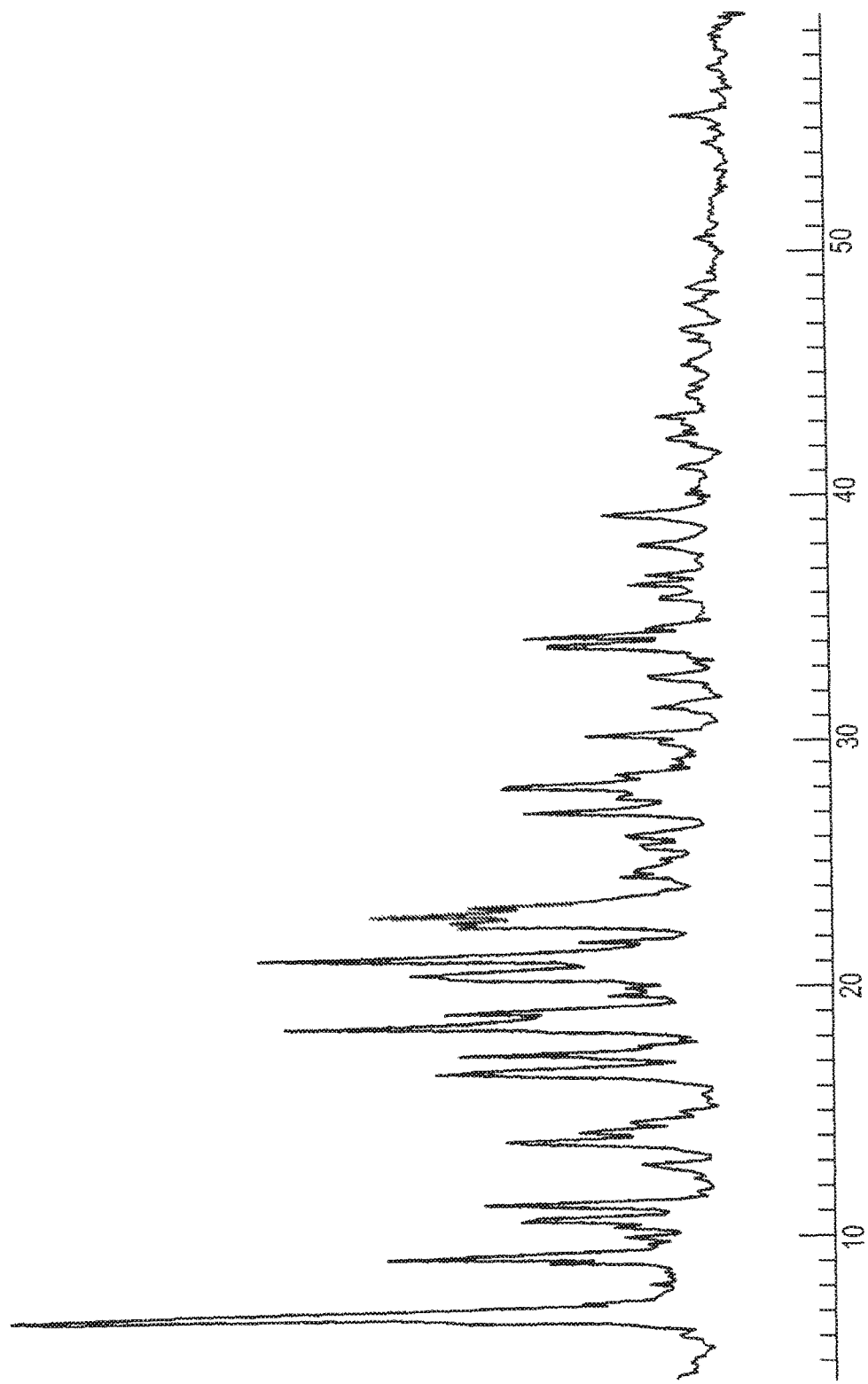

The X-ray powder diffraction is a technique to characterise polymorphic forms including pseudopolymorphs of compound of formula (X) and to differentiate solvate crystal forms from other crystal and non-crystal forms of compound of formula (X). As such, X-ray powder diffraction spectra were collected on a Phillips PW 1050/80 powder diffractometer, model Bragg-Brentano. Powders of Form A (1:1), around 200 mg each sample, were packed in 0.5 mm glass capillary tubes and were analysed according to a standard method in the art. The X-ray generator was operated at 45 Kv and 32 mA, using the copper Kα line as the radiation source. There was no rotation of the sample along the chi axis and data was collected between 4 and 60° 2-theta step size. Form A (1:1) has the characteristic two-theta angle positions of peaks as shown in FIGS. 1, 2 and 3 at: 7.04°±0.5°, 9.24°±0.5°, 9.96°±0.5°, 10.66°±0.5°, 11.30°±0.5°, 12.82°±0.5°, 13.80°±0.5°, 14.56°±0.5°, 16.66°±0.5°, 17.30°±0.5°, 18.28°±0.5°, 19.10°±0.5°, 20.00°±0.5°, 20.50°±0.5°, 21.22°±0.5°, 22.68°±0.5°, 23.08°±0.5°, 23.66°±0.5°, 25.08°±0.5°, 25.58°±0.5°, 26.28°±0.5°, 27.18°±0.5°, 28.22°±0.5°, 30.20°±0.5°, 31.34°±0.5°, 32.68°±0.5°, 33.82°±0.5°, 39.18°±0.5°, 41.20°±0.5°, 42.06°±0.5°, and 48.74°±0.5°.

In another set of analytical experiments, X-ray single diffraction was applied to Form A (1:1), which resulted in the following crystal configuration, listed in the table below.

TABLE 1

Crystal Data

| | |
|---|---|
| Crystal shape | Prism |
| Crystal dimensions | 0.56 × 0.38 × 0.24 mm |
| Crystal color | Colorless |
| Space Group | P $2_1$ $2_1$ $2_1$ orthorhombic |
| Temperature | 293 K |
| Cell constants | a = 9.9882(6) Å |
| | b = 16.1697(8) Å |
| | c = 19.0284(9) Å |

TABLE 1-continued

| | |
|---|---|
| | alpha (α) = 90° |
| | beta (β) = 90° |
| | gamma (γ) = 90° |
| Volume | 3158.7(3) Å³ |
| Molecules/unit cell (Z) | 4 |
| Density, in Mg/m³ | 1.248 |
| μ (linear absorption coefficient) | 1.340 mm⁻¹ |
| F(000) | 1272 |
| Intensity Measurements | |
| Diffractometer | Siemens P4 |
| Radiation | Cu Kα (λ = 1.54184 Å) |
| Temperature | ambient |
| 2θ$_{max}$ | 138.14° |
| Correction | Empirical via Ψ-scans |
| Number of Reflections Measured | Total: 3912 |
| Structure Solution and Refinement | |
| Number of Observations | 3467 [F² > 2 σ(F²)] |
| Residual (R) | 0.0446 |

Figure 4:
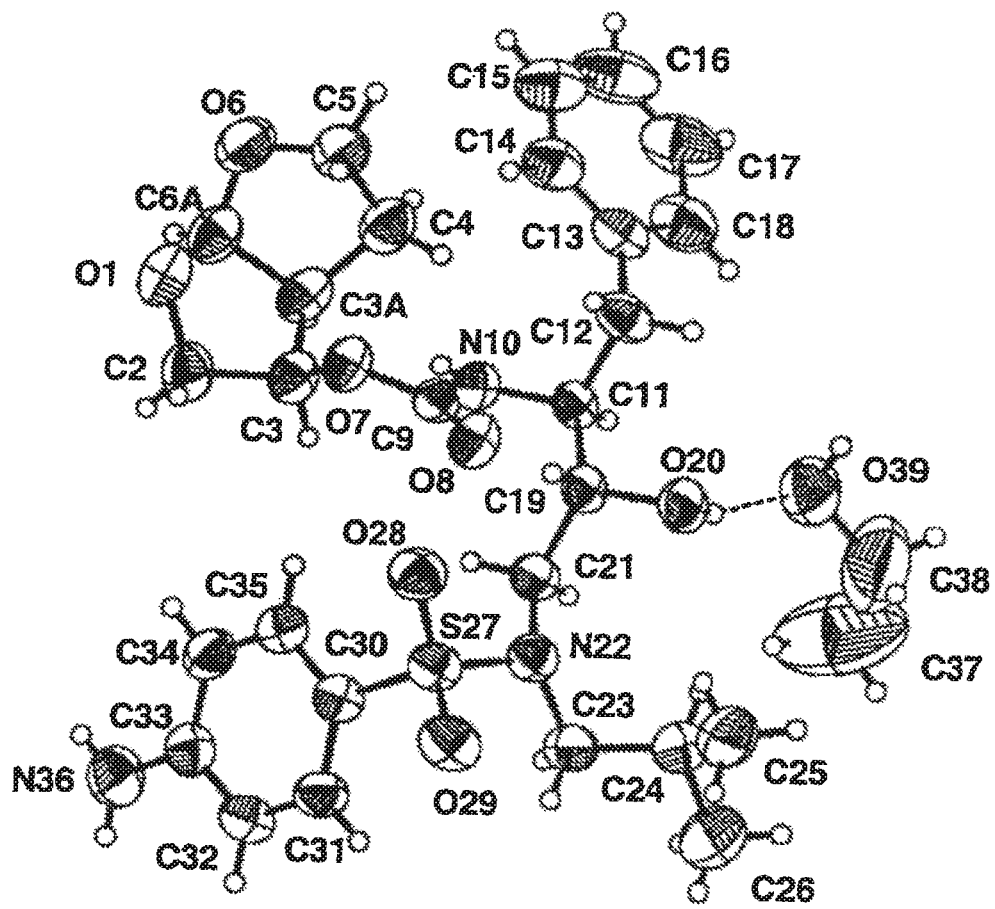
FIG. 4 depicts Form A (1:1) in three dimensions with the atoms identified.

The resulting three-dimensional structure of Form A (1:1) is depicted in FIG. 4.

Table 2 shows the atomic coordinates (×10⁴) and equivalent isotropic displacement parameters (Å²×10³) for Form A (1:1). Atoms are numbered as exhibited in FIG. 4. The x, y and z fractional coordinates indicate the position of atoms relative to the origin of the unit cell. U(eq) is defined as one third of the trace of the orthogonalized $U_{ij}$ tensor.

| | x | y | z | U(eq) |
|---|---|---|---|---|
| O1 | 7778(3) | 2944(2) | 9946(1) | 70(1) |
| C2 | 7171(4) | 3513(2) | 9487(2) | 64(1) |
| C3 | 6831(3) | 3046(2) | 8823(2) | 52(1) |
| C3A | 7953(3) | 2411(2) | 8793(2) | 55(1) |
| C4 | 7527(4) | 1533(2) | 8708(2) | 65(1) |
| C5 | 7425(5) | 1241(2) | 9457(2) | 70(1) |
| O6 | 8501(3) | 1642(2) | 9809(1) | 76(1) |
| C6A | 8582(4) | 2416(2) | 9534(2) | 62(1) |
| O7 | 5533(2) | 2702(1) | 8945(1) | 51(1) |
| O8 | 5168(2) | 2636(1) | 7768(1) | 53(1) |
| C9 | 4791(3) | 2534(1) | 8368(1) | 42(1) |
| N10 | 3590(2) | 2256(1) | 8562(1) | 43(1) |
| C11 | 2638(3) | 1916(2) | 8068(2) | 44(1) |
| C12 | 2223(3) | 1071(2) | 8310(2) | 58(1) |
| C13 | 3381(3) | 501(2) | 8387(2) | 56(1) |
| C14 | 3937(4) | 340(2) | 9038(2) | 67(1) |
| C15 | 4989(5) | −200(2) | 9111(3) | 80(1) |
| C16 | 5494(5) | −581(3) | 8530(3) | 96(2) |
| C17 | 4975(6) | −413(3) | 7881(3) | 98(2) |
| C18 | 3926(5) | 126(2) | 7810(2) | 78(1) |
| C19 | 1423(3) | 2464(2) | 7976(2) | 45(1) |
| O20 | 494(2) | 2112(1) | 7502(1) | 61(1) |
| C21 | 1829(3) | 3307(2) | 7740(2) | 48(1) |
| N22 | 699(3) | 3880(1) | 7721(1) | 49(1) |
| C23 | 521(4) | 4312(2) | 7048(2) | 58(1) |
| C24 | −61(4) | 3785(2) | 6473(2) | 67(1) |
| C25 | −1453(5) | 3497(3) | 6654(2) | 86(2) |
| C26 | −47(7) | 4247(3) | 5779(2) | 102(2) |
| S27 | 510(1) | 4414(1) | 8440(1) | 50(1) |
| O28 | 572(3) | 3860(1) | 9015(1) | 61(1) |
| O29 | −693(2) | 4873(1) | 8345(1) | 65(1) |
| C30 | 1854(3) | 5080(2) | 8509(2) | 50(1) |
| C31 | 1803(3) | 5825(2) | 8159(2) | 54(1) |
| C32 | 2871(4) | 6341(2) | 8195(2) | 56(1) |
| C33 | 4033(4) | 6133(2) | 8564(2) | 55(1) |
| C34 | 4063(4) | 5385(2) | 8909(2) | 59(1) |
| C35 | 2998(4) | 4869(2) | 8883(2) | 56(1) |
| N36 | 5076(3) | 6667(2) | 8596(2) | 72(1) |
| C37 | 1920(10) | 2231(7) | 5258(4) | 232(6) |
| C38 | 1310(10) | 1590(6) | 5564(4) | 191(5) |
| O39 | 1768(4) | 1393(2) | 6249(2) | 94(1) |

Table 3 shows the anisotropic displacement parameters (Å²×10³) for Form A (1:1). The anisotropic displacement factor exponent takes the formula:

$$-2\pi^2[h^2 a^{*2} U_{11} + \ldots + 2\, h\, k\, a^* b^* U_{12}]$$

| | $U_{11}$ | $U_{22}$ | $U_{33}$ | $U_{23}$ | $U_{13}$ | $U_{12}$ |
|---|---|---|---|---|---|---|
| O1 | 65(2) | 89(2) | 55(1) | −4(1) | −12(1) | −3(1) |
| C2 | 53(2) | 68(2) | 71(2) | −7(2) | −8(2) | −11(2) |
| C3 | 38(2) | 63(2) | 55(2) | 4(1) | −2(1) | −12(1) |
| C3A | 37(2) | 78(2) | 49(1) | 9(1) | 1(1) | −3(2) |
| C4 | 61(2) | 74(2) | 61(2) | −4(2) | −6(2) | 10(2) |
| C5 | 72(3) | 67(2) | 71(2) | 8(2) | −11(2) | −7(2) |
| O6 | 78(2) | 80(2) | 70(1) | 16(1) | −21(1) | −8(2) |
| C6A | 47(2) | 80(2) | 59(2) | 5(2) | −6(2) | −7(2) |
| O7 | 34(1) | 69(1) | 50(1) | 0(1) | −1(1) | −9(1) |
| O8 | 42(1) | 68(1) | 50(1) | 3(1) | 2(1) | −12(1) |
| C9 | 35(2) | 41(1) | 49(1) | 1(1) | −3(1) | 3(1) |
| N10 | 31(1) | 50(1) | 49(1) | −1(1) | 1(1) | −2(1) |
| C11 | 32(2) | 41(1) | 57(1) | −4(1) | 0(1) | −2(1) |
| C12 | 44(2) | 42(1) | 87(2) | 2(1) | 2(1) | −4(1) |
| C13 | 50(2) | 39(1) | 78(2) | 0(1) | 8(2) | 0(1) |
| C14 | 64(2) | 56(2) | 80(2) | 0(2) | 5(2) | 9(2) |
| C15 | 68(3) | 72(2) | 100(3) | 18(2) | 7(2) | 12(2) |
| C16 | 77(3) | 68(2) | 143(4) | 26(3) | 34(3) | 28(2) |
| C17 | 114(4) | 72(2) | 109(3) | −6(2) | 32(3) | 38(3) |
| C18 | 89(3) | 60(2) | 85(2) | −4(2) | 10(2) | 10(2) |
| C19 | 30(2) | 44(1) | 61(1) | −3(1) | −5(1) | −5(1) |
| O20 | 44(1) | 56(1) | 83(1) | −6(1) | −18(1) | −6(1) |
| C21 | 36(2) | 42(1) | 64(2) | 2(1) | −4(1) | −1(1) |
| N22 | 42(1) | 47(1) | 57(1) | 1(1) | 0(1) | 3(1) |
| C23 | 59(2) | 50(1) | 64(2) | 7(1) | −8(2) | 1(2) |
| C24 | 79(3) | 59(2) | 62(2) | 1(1) | −11(2) | 6(2) |
| C25 | 75(3) | 83(2) | 101(3) | 6(2) | −30(3) | −5(2) |
| C26 | 143(5) | 99(3) | 65(2) | 14(2) | −15(3) | −6(3) |
| S27 | 44(1) | 47(1) | 61(1) | 2(1) | 2(1) | 1(1) |
| O28 | 64(2) | 58(1) | 61(1) | 9(1) | 3(1) | −7(1) |
| O29 | 46(1) | 58(1) | 92(2) | −4(1) | 6(1) | 10(1) |
| C30 | 50(2) | 46(1) | 54(1) | 2(1) | 1(1) | 1(1) |
| C31 | 50(2) | 48(1) | 64(2) | 6(1) | −4(2) | 6(1) |
| C32 | 59(2) | 45(1) | 65(2) | 4(1) | 2(2) | 1(1) |
| C33 | 57(2) | 55(2) | 52(1) | −4(1) | 1(1) | −3(1) |
| C34 | 56(2) | 63(2) | 59(2) | 6(1) | −13(2) | −3(2) |
| C35 | 63(2) | 52(1) | 53(1) | 5(1) | −8(2) | −2(2) |
| N36 | 67(2) | 70(2) | 80(2) | 4(2) | −5(2) | −19(2) |
| C37 | 290(10) | 260(10) | 145(7) | 68(7) | 67(8) | 120(10) |
| C38 | 280(10) | 187(7) | 104(4) | 1(5) | −53(6) | −80(10) |
| O39 | 99(2) | 91(2) | 93(2) | 1(2) | −13(2) | −28(2) |

Figure 5:
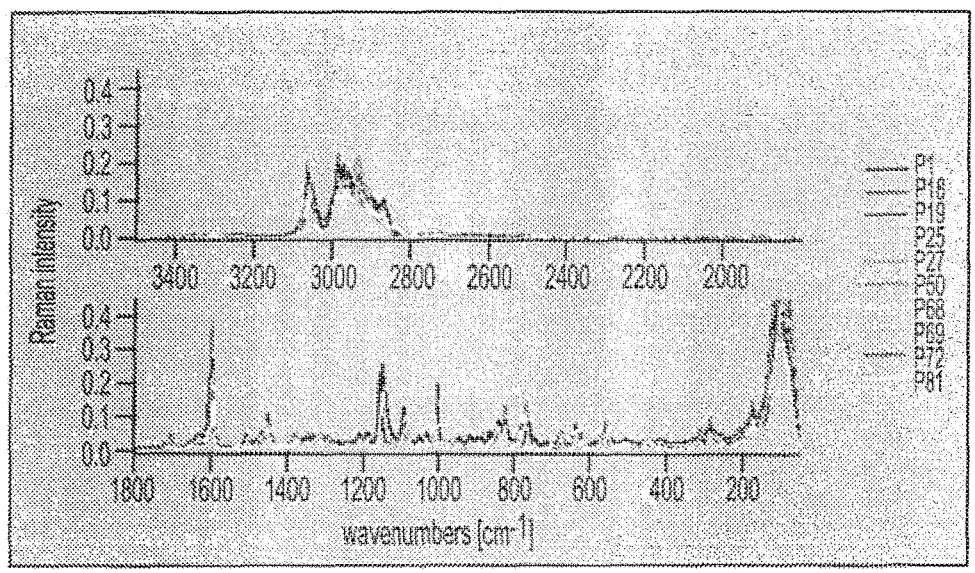
FIG. 5 is a comparison of the Raman spectra of Forms A, B, D, E, F, H, (1:1) and the amorphous form at the carbonyl stretching region of 1800-100 $cm^{-1}$ and the region 3300-2000 $cm^{-1}$.
Figure 6:
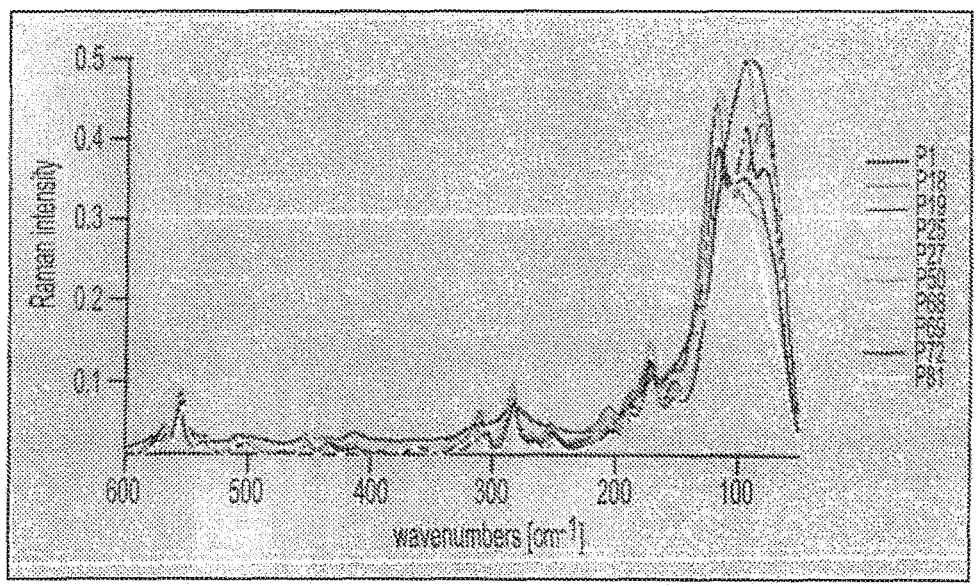
FIG. 6 is a comparison of the expanded Raman spectra of Forms A, B, D, E, F, H, (1:1) and the amorphous form at the carbonyl stretching region of 600-0 $cm^{-1}$.
Figure 7:
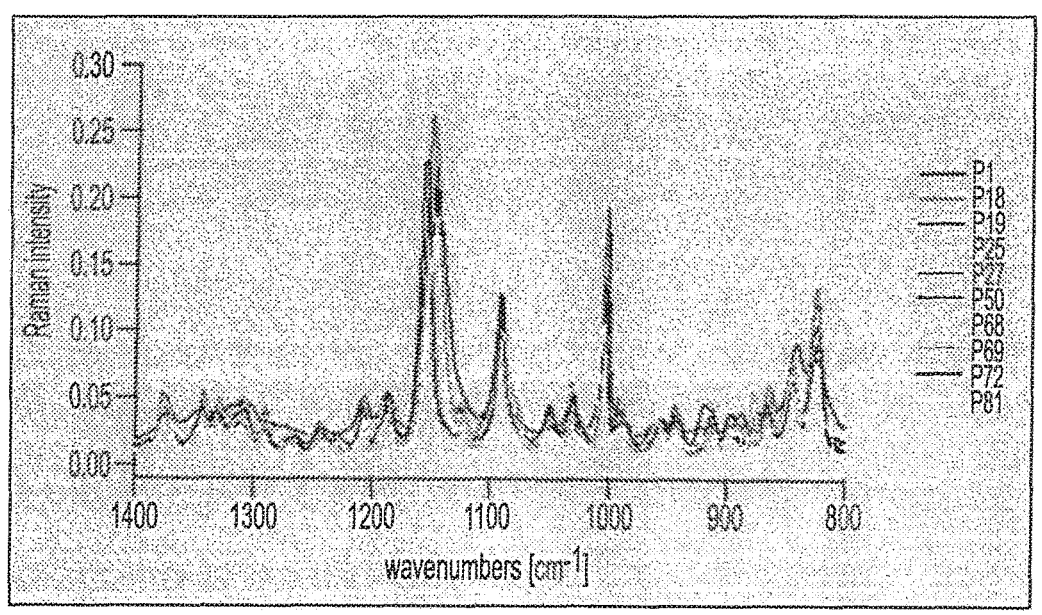
FIG. 7 is a comparison of the expanded Raman spectra of Forms A, B, D, E, F, H, (1:1) and the amorphous form at the carbonyl stretching region of 1400-800 $cm^{-1}$.

Raman spectroscopy has been widely used to elucidate molecular structures, crystallinity and polymorphism. The low-frequency Raman modes are particularly useful in distinguishing different molecular packings in crystal. As such, Raman spectra were recorded on a Bruker FT-Raman RFS100 spectrometer equipped with a photomultiplier tube and optical multichannel detectors. Samples placed in quartz capillary tubes were excited by an argon ion laser. The laser power at the samples was adjusted to about 100 mW and the spectral resolution was about 2 cm⁻¹. It was found that Forms A, B, D, E, F, and H, (1:1) and the amorphous form have the Raman spectra which appear in FIGS. 5, 6, and 7.

In addition, Forms A and B were characterized using a μATR (Micro-Attenuated Total Reflectance) accessory (Harrick Split-Pea with Si crystal). The infrared spectra were obtained with a Nicolet Magna 560 FTIR spectrophotometer, a Ge on KBr beamsplitter, and a DTGS with KBr windows detector. Spectra were measured at 1 cm⁻¹ resolution and 32 scans each, in a wavelength range of from 4000 to 400 cm⁻¹, and application of baseline correction. The wavenumbers for Form A obtained are exhibited in the following Table 4.

TABLE 4

Wavenumbers (cm$^{-1}$) and relative intensities of absorption bands ([1])

Figure 9:
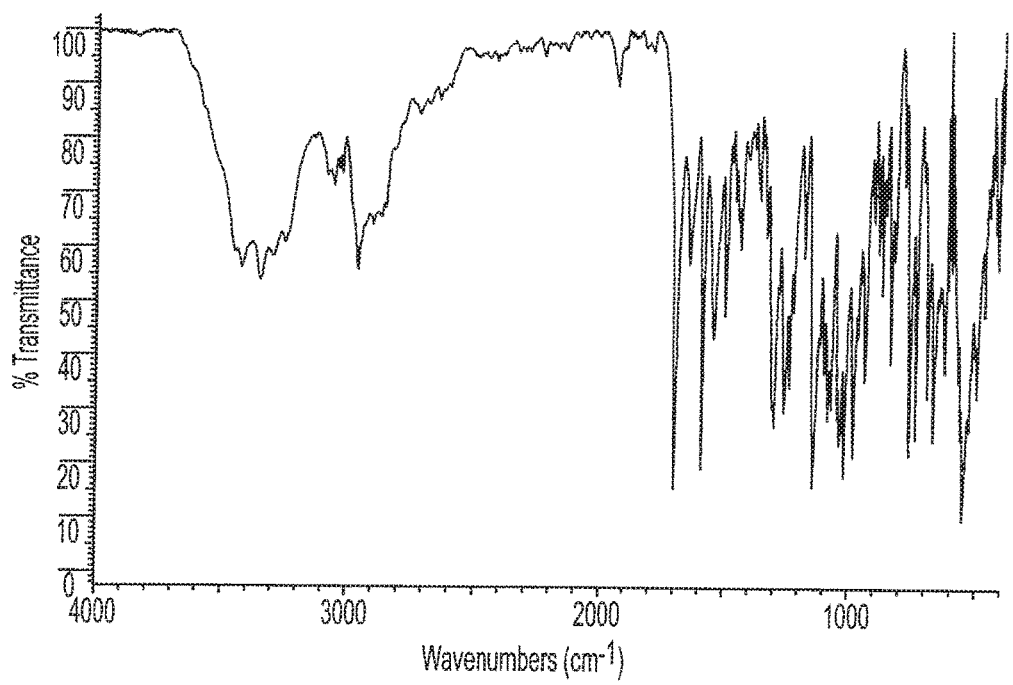
FIG. 9 is the Infrared (IR) spectrum that reflects the vibrational modes of the molecular structure of Form A as a crystalline product

3454w, 3429w, 3354w, 3301w, 3255w, 3089w, 3060w, 3041w, 3028w
2964w, 2905w, 2875w, 2856w, 2722vw, 2684vw, 2644vw, 2603vw, 2234vw
1704s, 1646w, 1595s, 1550m, 1503m, 1466w, 1453w, 1444w, 1413w
1373w, 1367w, 1340w, 1324m, 1314m, 1306m, 1290w, 1266m, 1244m, 1229m
1187w, 1146s, 1124m, 1104m, 1090m, 1076m, 1052m, 1042s, 1038m, 1024s
987s, 971m, 944m, 909w, 890w, 876m, 841m, 792w, 768s, 742s, 732w, 697m, 674s, 645w, 630m
598w, 593w, 574m, 564s, 553vs, 538m, 533m, 531m, 526m, 508m, 501m, 491m, 471w, 458w, 445w, 442w, 436w, 428w, 418w vs = very strong,
s = strong,
m = medium,
w = weak,
vw = very weak,
br = broad The IR spectrum in FIG. 9 reflects the vibrational modes of the molecular structure as a crystalline product.

The wavenumbers obtained for Form B are exhibited in the following Table 5.

TABLE 5

Wavenumbers (cm$^{-1}$) and relative intensities of absorption bands([1])

Figure 10:
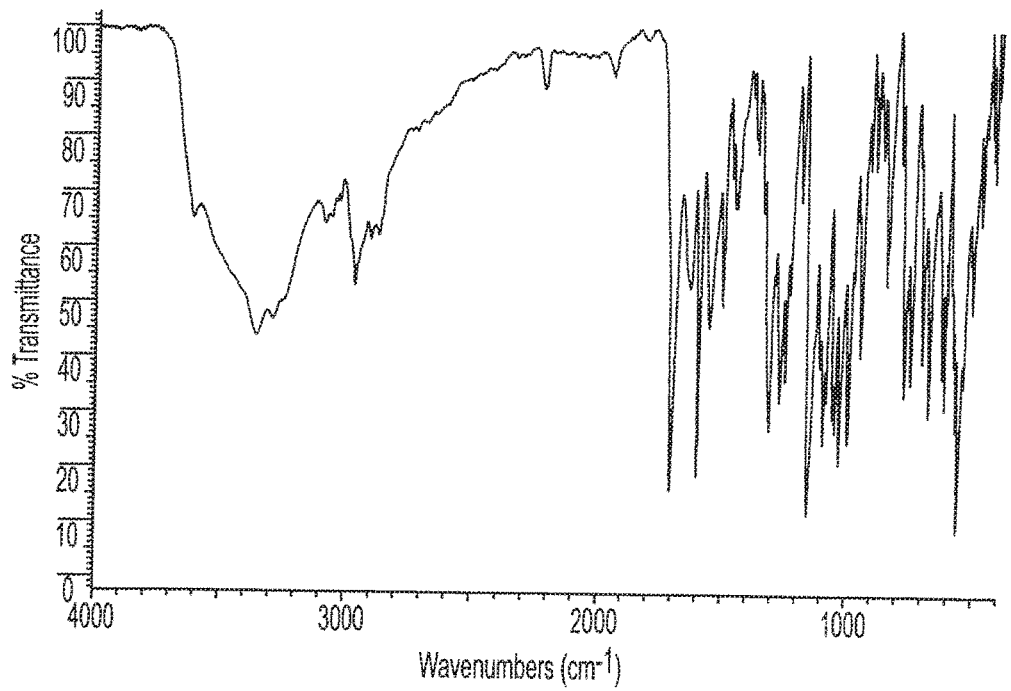
FIG. 10 is the IR spectrum that reflects the vibrational modes of the molecular structure of Form B as a crystalline product

3614w, 3361m, 3291m, 3088w, 3061w, 3043w, 3028w
2967w, 2905w, 2872w, 2222vw
1703s, 1631w, 1595s, 1553m, 1502w, 1467w, 1453w, 1444w, 1436w
1388vw, 1374vw, 1366w, 1355vw, 1340w, 1308m, 1291w, 1267m, 1245m
1187w, 1148s, 1125m, 1105m, 1091m, 1077m, 1052m, 1044m, 1025s
990m, 972w, 944m, 912w, 891w, 876vw, 862w, 843m, 836w, 792w, 769m, 757w, 743m, 717w, 699m, 672m
598w, 591w, 585w, 576m, 566m, 553vs, 536m, 509w, 502m, 484w, 471w, 432vw, 425w, 418w ([1])vs = very strong, s = strong, m = medium, w = weak, vw = very weak, br = broad The IR spectrum in FIG. 10 reflects the vibrational modes of the molecular structure of Form B as a crystalline product.

Following the same analytical IR method, Form B and the amorphous form were also characterised and compared with Form A, as shown in FIGS. 11 to 14. IR spectra of the different physical forms showed distinct spectral differences, most relevant are those in Table 6:

TABLE 6

Wavenumbers (cm$^{-1}$) and relative intensities of absorption bands([1])

| Form A | Form B | Amorphous form |
|---|---|---|
| 3454m, 3429m, 3353m, 3255m, 3089w, 3060m, 3041w, 3028w | 3615m, 3356m, 3291m, 3089m, 3061m, 3043w, 3027w | 3462m, 3362m, 3249m, 3062m, 3026m |
| 2963m, 2905m, 2869m, 2856m | 2966m, 2905m, 2873m | 2959m, 2871m |
| 1704s, 1646m, 1596s, 1549s, 1503s | 1703s, 1630m, 1595s, 1552s, 1502m | 1704s, 1628s, 1596s, 1525s, 1502s |
| 1306s, 1266s, 1244s | 1308s, 1267s, 1245s | 1312s, 1259s |
| 1146s, 1104s, 1090s, 1076s, 1052s, 1042s, 1038s, 1023s | 1148s, 1105s, 1090s, 1077s, 1052s, 1044s, 1024s | 1143s, 1090s, 1014s |
| 987s, 971s, 954s, 945s, 912m, 909m, 891s, 876s, 841s, 827s | 989s, 972s, 944s, 925m, 915m, 912s, 891s, 862s, 843s | 960s, 953s, 950s, 944s, 937s, 922s, 832s |
| 792m, 768s, 742s, 697s, 674s | 792s, 769s, 744s, 699s, 672s | 750br, 702s, 672s |

([1])s = strong, m = medium, w = weak, vw = very weak, br = broad

The physical Forms A, B, and amorphous form are identified through spectral interpretation, focused on absorption bands specific for each form. Unique and specific spectral differences between forms are noticed in 3 spectral ranges: from 3750 to 2650 cm$^{-1}$ (range 1), from 1760 to 1580 cm$^{-1}$ (range 2) and from 980 to 720 cm$^{-1}$ (range 3).

Range 1 (from 3750 to 2650 cm$^{-1}$)

Figure 11:
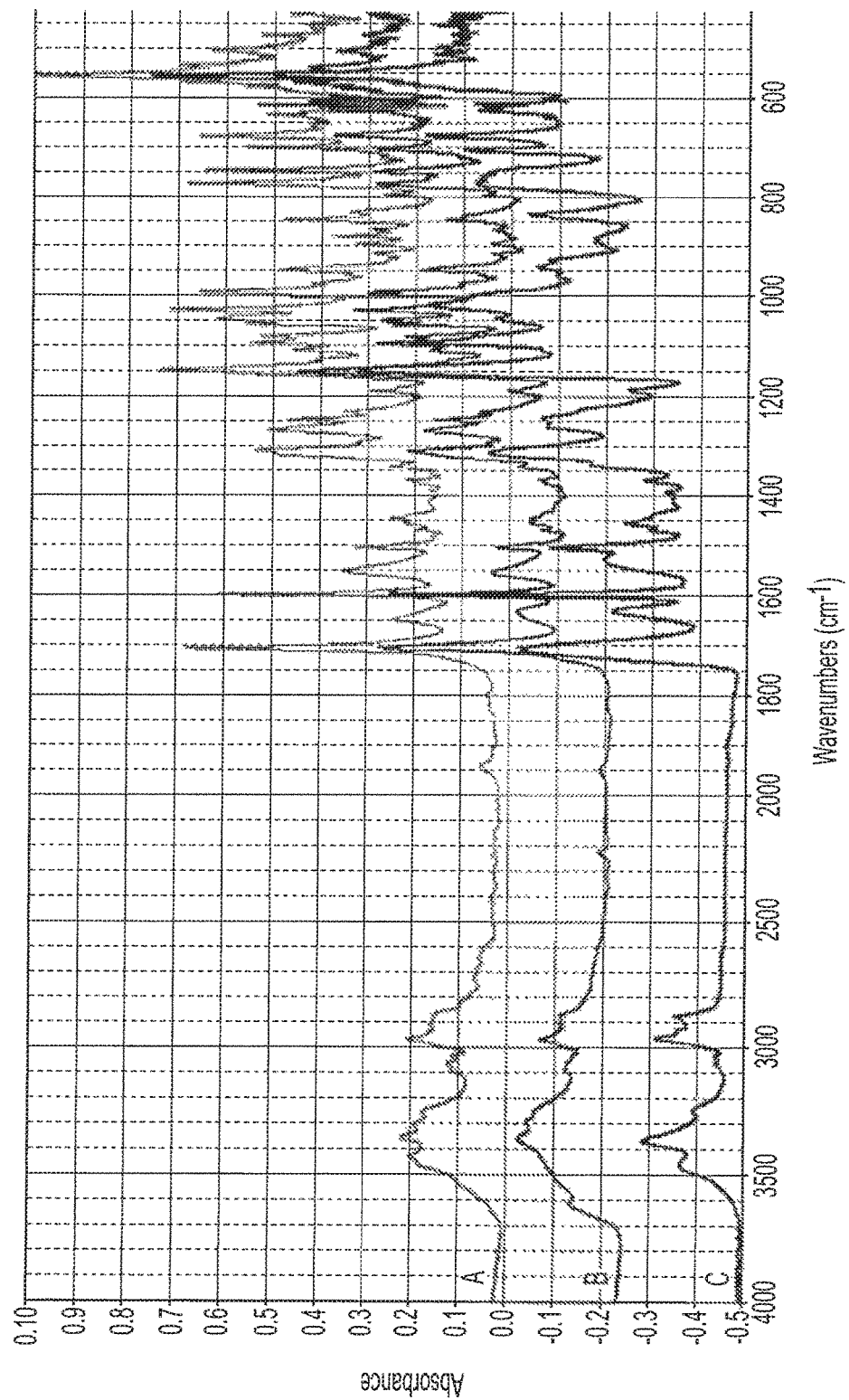
FIG. 11: IR spectrum of forms A, B, and amorphous form, at spectral range 4000 to 400 $cm^{-1}$.

FIG. 11: Form A shows a double band with absorption maxima at 3454 cm$^{-1}$ and 3429 cm$^{-1}$. Form B shows a single absorption band at 3615 cm$^{-1}$ and amorphous form shows a single absorption band at 3362 cm$^{-1}$.

Range 2 (from 1760 to 1580 cm$^{-1}$)

Figure 12:
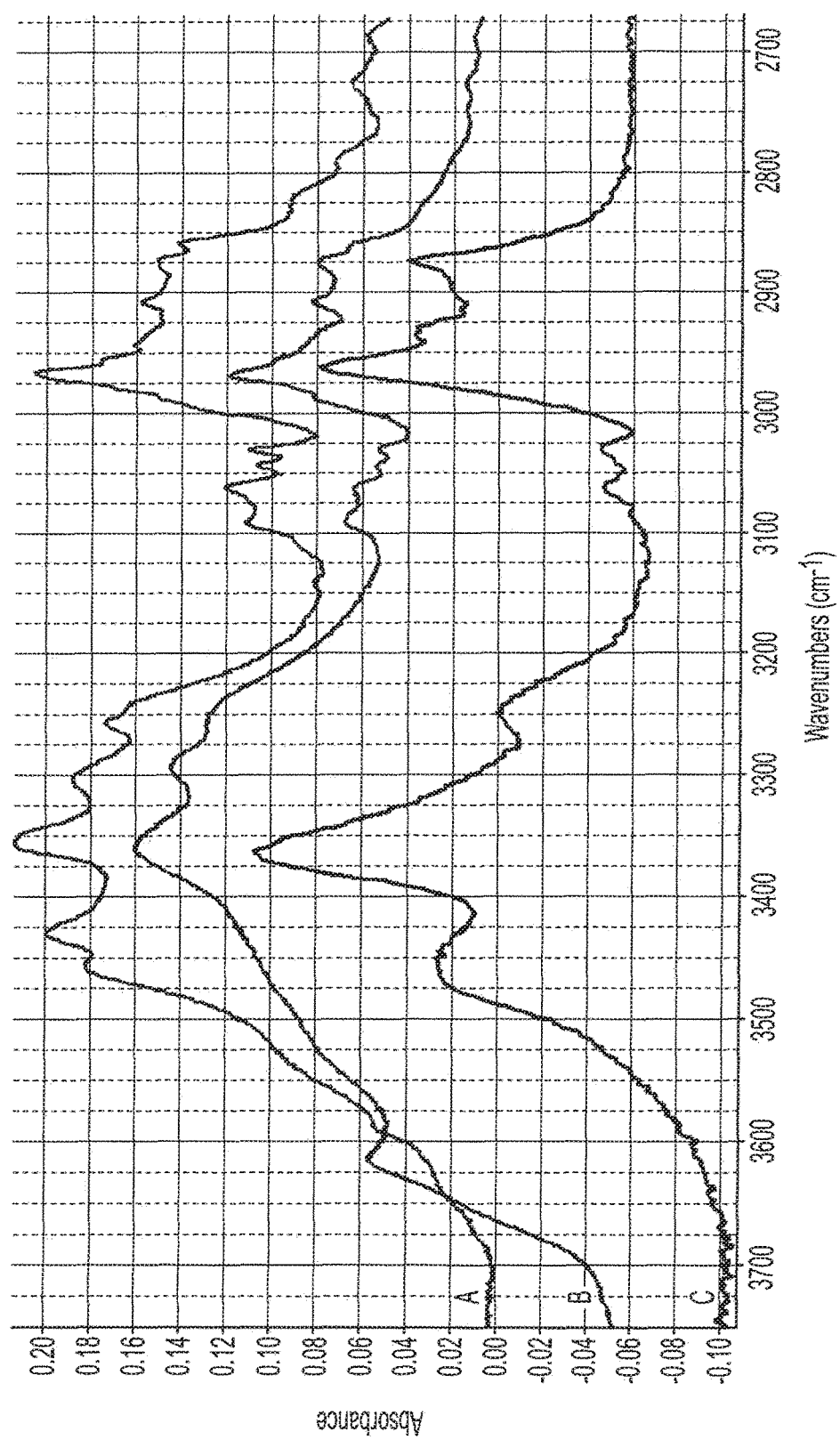
FIG. 12: IR spectrum of forms A, B, and amorphous form, at spectral range 3750 to 2650 $cm^{-1}$

FIG. 12: Form A shows a single absorption band at 1646 cm$^{-1}$, Form B shows a single absorption band at 1630 cm$^{-1}$ and amorphous form shows a single absorption band at 1628 cm$^{-1}$ with a clearly higher intensity compared to the Form B band. Additionally, amorphous form shows a less intense, broad band at 1704 cm$^{-1}$ compared to both forms A and B bands at about 1704 cm$^{-1}$.

Range 3 (from 980 to 720 cm$^{-1}$)

Figure 13:
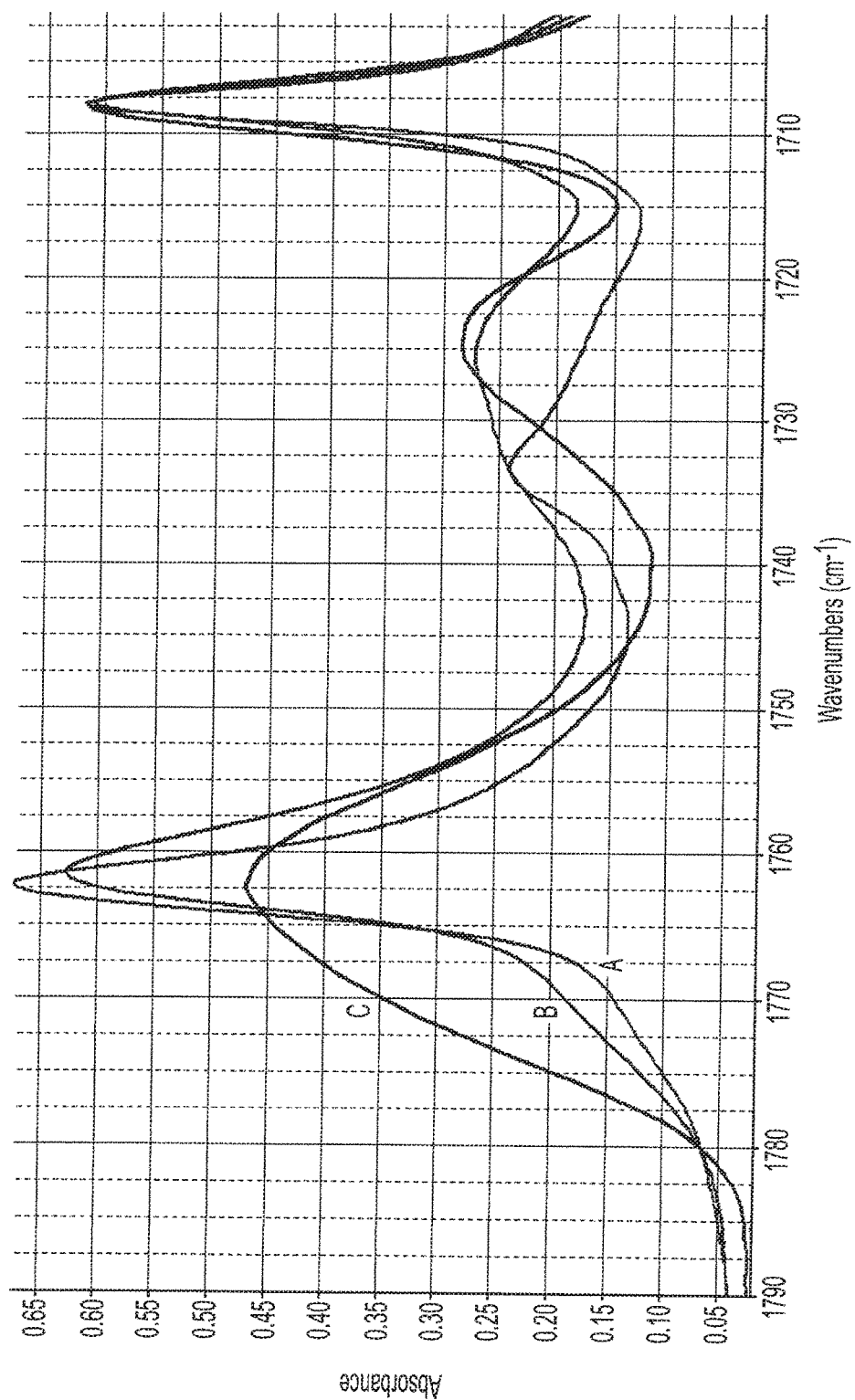
FIG. 13: IR spectrum of forms A, B, and amorphous form, at spectral range 1760 to 1580 $cm^{-1}$
Figure 14:
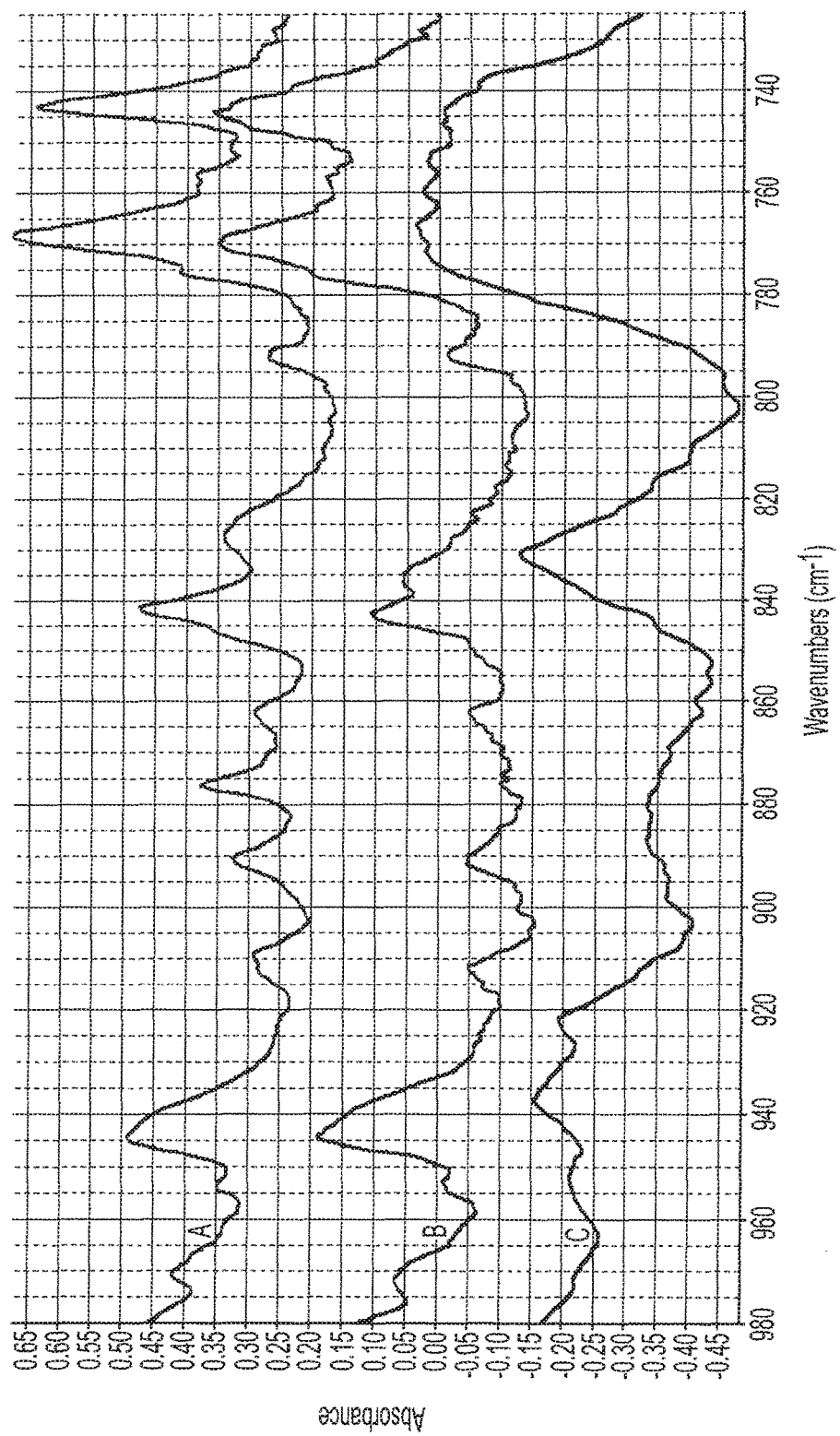
FIG. 14: IR spectrum of forms A, B, and amorphous form, at spectral range 980 to 720 $cm^{-1}$ In FIGS. 11, 12, 13 and 14, curve A corresponds to Form A, curve B corresponds to Form B, and curve C corresponds to the amorphous form.

FIG. 13: Form A shows a distinct set of 5 absorption bands at 911, 890, 876, 862 and 841 cm$^{-1}$. Form B shows a similar set but the 876 cm$^{-1}$ band is missing. Amorphous form shows a single broad band at about 750 cm$^{-1}$, both forms A and B show two maxima at about 768 cm$^{-1}$ and 743 cm$^{-1}$.

Thermomicroscopy is another useful technique in the study of solid-state kinetics. The kinetics of nucleation processes from solutions or melts, including the analysis of the nucleation speed, can be quantified. The simplest and most widely used method is the melting point determination. As such, a Mettler model FP 82 controller with heating stage was used on a Leitz microscope. A few particles of Form A were placed on a glass slide and observed while heating at 10° C. per minute. The melting range for Form A (1:1) was found to be between 90° and 110° C.

On another means of characterization, the solubility of Form A (1:1) was also a matter subject to study. Its solubility in different solvents at approximate 23° C. was determined to be as follows:

TABLE 7

Approximate solubility for Form A (1:1), in mg/ml

| Solvent | Approximate solubility Form A (mg/ml) |
| --- | --- |
| Acetone | 106-211 |
| Dichloromethane | 105-209 |
| 1-Methoxy-2-propanol | 160-213 |
| Ethylmethylketone | 102-204 |
| Ethylacetate | 71-107 |
| Ethanol absolute | <3.4 |
| Heptane | <3.4 |
| Water | <3.5 |
| Isopropylether | <3.4 |
| Methacyanate | >200 |
| Methanol | <3.4 |
| 2-Propanol | <3.4 |
| Tetrahydrofurane | 102-203 |
| Toluene | <3.5 |

Further solubility investigations were performed in function of pH. As such, the aqueous solubilities of Form. A (1:1) were measured in solvents with different pH. An excess of the solute was equilibrated with the solvent at 20° C. for at least 24 hours. After removing the undissolved compound, the concentration in solution was determined using UV spectrometry.

TABLE 8

Solubility for Form A (1:1) in function of pH

| Solvent | Solubility (mg/100 ml solution) |
| --- | --- |
| Water | 16 (pH 5.9) |
| Buffer pH 2 (citrate/HCl) | 18 (pH 2.0) |
| Buffer pH 3 (citrate/HCl) | 10 (pH 3.0) |
| Buffer pH 4 (citrate/HCl) | 9 (pH 4.0) |
| 0.01N HCl | 18 (pH 2.1) |
| 0.1N HCl | 83 (pH 1.1) |
| 1.0N HCl | 620 (pH 0.2) |

Solubility of Form A (1:1) in function of HPβCD (hydroxypropyl-β-cyclodextrin) was measured. An excess of product was equilibrated with the solvent during 2 days at 20° C. After removing the undissolved compound, the concentration in solution was determined using UV spectrometry.

TABLE 9

Solubility for Form A (1:1) in function of HPβCD

| solvent | Solubility in mg/ml solution |
| --- | --- |
| Water | 0.16 (pH = 5.9) |
| 5% HPβCD in water | 2.4 (pH = 5.8) |
| 10% HPβCD in water | 6.5 (pH = 6.0) |
| 20% HPβCD in water | 17 (pH = 6.0) |
| 40% HPβCD in water | 40 (pH = 5.9) |

In a second aspect, the present invention relates to processes for preparing pseudopolymorphs. Pseudopolymorphs of compound of formula (X) are prepared by combining compound of formula (X) with an organic solvent, or water, or mixtures of water and water miscible organic solvents, applying any suitable technique to induce crystallization, and isolating the desired pseudopolymorphs.

By techniques for inducing crystallization are to be understood those processes for the production of crystals, which include amongst others, dissolving or dispersing compound of formula (X) in a solvent medium, bringing the solution or dispersion of compound of formula (X) and the solvent(s) to a desired concentration, bringing the said solution or dispersion to a desired temperature, effecting any suitable pressure, removing and/or separating any undesired material or impurities, drying the formed crystals to obtain the pseudopolymorphs in a solid state, if such state is desired.

Bringing the solution or dispersion of compound of formula (X) and solvents to a desired concentration does not necessarily imply an increase in the concentration of compound of formula (X). In certain cases, a decrease or no change in concentration could be preferable. By bringing the said solution or dispersion to a desired temperature, one will understand the acts of heating, cooling or leaving at ambient temperature.

The techniques used for obtaining a desired concentration are those common in the art, for instance, evaporation by atmospheric distillation, vacuum distillation, fractioned distillation, azeotropic distillation, film evaporation, other techniques well known in the art and combinations thereof. An optional process for obtaining a desired concentration could as well involve the saturation, of the solution of compound of formula (X) and solvent, for example, by adding a sufficient volume of a non-solvent to the solution to reach the saturation point. Other suitable techniques for saturating the solution include, by way of example, the introduction of additional compound of formula (X) to the solution and/or evaporation of a portion of the solvent from the solution. As referred to herein, saturated solution encompasses solutions at their saturation points or exceeding their saturation points, i.e. supersaturated.

Removing and/or separating any undesired material or impurities may be performed by purification, filtering, washing, precipitation or similar techniques. Separation, for example, can be conducted by known solid-liquid separation techniques. Filtering procedures known to those skilled in the art can as well be used in the present process. The filtrations can be performed, amongst other methods, by centrifugation, or using Buchner style filter, Rosenmund filter or plates, or frame press. Preferably, in-line filtration or safety filtration may be advantageously intercalated in the processes disclosed above, in order to increase the purity of the resulting pseudopolymorphic form. Additionally, filtering agents such as silica gel, Arbocel®, dicalite diatomite, or the like, may also be employed to separate impurities from the crystals of interest.

Crystals obtained may be also dried, and such drying process may optionally be used in the different crystallization passages, if more than one crystallization passage is applied. Drying procedures include all techniques known to those skilled in the art, such as heating, applying vacuum, circulating air or gas, adding a desiccant, freeze-drying, spray-drying, evaporating, or the like, or any combination thereof.

Processes for crystallization of pseudopolymorphs of compound of formula (X) embrace multiple combinations of techniques and variations thereof. As such, and by way of example, crystallization of pseudopolymorphs of compound of formula (X) may be executed by dissolving or dispersing compound of formula (X) at a suitable temperature in the solvent whereby portion of the said solvent evaporates increasing the concentration of the compound of formula (X) in the said solution or dispersion, cooling the said mixture, and optionally washing and/or filtering and drying resulting solvate crystals of compound of formula (X). Optionally, pseudopolymorphs of compound of formula (X) may be prepared by dissolving or dispersing compound of formula (X) in a solvent medium, cooling said solution or dispersion and subsequently filtering and drying the obtained pseudopolymorph. Another example of preparation of solvates of compound of formula (X) could be by saturating compound of formula (X) in the solvent medium, and optionally filtering, washing and drying obtained crystals.

Crystal formation may as well involve more than one crystallization process. In certain cases, one, two or more extra crystallization steps may be advantageously performed for different reasons, such as, to increase the quality of the resulting solvate. For instance, pseudopolymorphs of the present invention could also be prepared by adding a solvent to an initial starting base material of compound of formula (X), stirring the solution at a fixed temperature until the substances would be fully solved, concentrating the solution by vacuum distillation, and cooling. A first crystallization would take place and the formed crystals would be newly washed with a solvent, and followed by dissolution of compound of formula (X) with the solvent to form the desired pseudopolymorph. Recrystallization of the reaction mixture would occur, followed by a cooling step from reflux. The formed pseudopolymorph would optionally be filtered and allowed to dry.

By dissolving or dispersing compound of formula (X) in the organic solvent, water or a mixture of water and water miscible organic solvents, one may obtain different degrees of dispersion, such as suspensions, emulsions, slurries or mixtures; or preferably obtain homogeneous one-phase solutions.

Optionally, the solvent medium may contain additives, for example one or more dispersing agents, surfactants or other additives, or mixtures thereof of the type normally used in the preparation of crystalline suspensions and which are well documented in the literature. The additives may be advantageously used in modifying the shape of crystal by increasing the leniency and decreasing the surface area.

The solvent medium containing the solution may optionally be stirred for a certain period of time, or vigorously agitated using, for example, a high shear mixer or homogeniser or a combination of these, to generate the desired droplet size for the organic compound.

Examples of organic solvents useful for the present invention include $C_1$-$C_4$ alcohols such as methanol, ethanol, isopropanol, butanol, 1-methoxy-2-propanol, and the like; $C_1$-$C_4$ chloroalkanes such as dichloromethane; $C_1$-$C_4$ ketones such as acetone; $C_1$-$C_4$ ethers such as anisole, and the like; cycloethers such as tetrahydrofuran; $C_1$-$C_4$ esters such as ethylacetate; $C_1$-$C_4$ sulfonates such as mesylate, ethanesulfonate, butanesulfonate, 2-methyl-1-propanesulfonate; and the like.

Examples of mixtures of water and water miscible organic solvents include, mixtures of water with all organic solvents listed above provided they are miscible in water, e.g. ethanol/water, for instance in a 50/50 ratio.

Preferred solvents are those pharmaceutically acceptable solvents. However, pharmaceutically non-acceptable solvents may also find their use in the preparation of pharmaceutically acceptable pseudopolymorphs.

In a preferred method, the solvent is a pharmaceutically acceptable solvent since it results in a pharmaceutically acceptable pseudopolymorph. In a more preferred method, the solvent is ethanol.

In a particular embodiment, pharmaceutically acceptable pseudopolymorphs of compound of formula (X) can be prepared starting from pseudopolymorphic forms of compound of formula (X), which may not be necessarily pharmaceutically acceptable. For instance, Form A may be prepared starting from Form J. Pseudopolymorphs may also be prepared starting from the amorphous form.

In the mixtures of water and water miscible organic solvents, the amount of water can vary from about 5% by volume to about 95% by volume, preferably from about 25% to about 75% by volume, more preferably from about 40% to about 60% by volume.

It should also be noted that the quality of selected organic solvent (absolute, denaturated, or other) also influences the resulting quality of the pseudopolymorph.

Control of precipitation temperature and seeding may be additionally used to improve the reproducibility of the crystallization process, the particle size distribution and form of the product. As such, the crystallization can be effected without seeding with crystals of the compound of the formula (X) or preferably in the presence of crystals of the compound of the formula (X), which are introduced into the solution by seeding. Seeding can also be effected several times at various temperatures. The amount of the seed material depends on the amount of the solution and can readily be determined by a person skilled in the art.

The time for crystallization in each crystallization step will depend on the conditions applied, the techniques employed and/or solvents used.

Breaking up the large particles or aggregates of particles after crystal conversion may additionally be performed in order to obtain a desired and homogeneous particle size. Accordingly, the solvate crystal forms of compound of formula (X) are optionally milled after undergoing conversion. Milling or grinding refers to physically breaking up the large particles or aggregates of particles using methods and apparatus well known in the art for particle size reduction of powders. Resulting particle sizes may range from millimeters to nanometers, yielding i.e. nanocrystals, microcrystals.

The yield of the preparation process of the pseudopolymorphs of compound of formula (X) may be 10% or more, a more preferred yield would vary from 40% to 100%.

Interestingly, the yield varies between 70% and 100%.

Suitably, pseudopolymorphs of the present invention have a purity greater than 90 percent. More suitably, the present pseudopolymorphs have a purity greater than 95 percent. Even more suitably, the present pseudopolymorphs have a purity greater than 99 percent.

In a third aspect, the present invention relates to a pharmaceutical formulation comprising a therapeutically effective amount of a pseudopolymorph of compound of formula (X), and a pharmaceutically acceptable carrier or diluent thereof.

In one embodiment, present invention relates to the use of pharmaceutically acceptable pseudopolymorphic forms of compound of formula (X), preferably Form A, in the manufacture of a medicament for treating diseases caused by retroviruses, such as HIV infections, for example, Acquired Immune Deficiency Syndrome (AIDS) and AIDS-related complex (ARC).

In another embodiment, present invention provides a method for the treatment of a retroviral infection, for example an HIV infection, in a mammal such as a human, which comprises administering to the mammal in need thereof an effective antiretroviral amount of a pharmaceutically acceptable pseudopolymorphic form of compound of formula (X), preferably Form A.

Present invention also relates to a method in which the treatment of a HIV viral infection comprises the reduction of HIV load. Present invention also relates to a method in which the treatment of said HIV viral infection comprises the increase of CD4+ cell count. Present invention relates as well to a method in which the treatment of said HIV viral infection comprises inhibiting HIV protease activity in a mammal.

Pharmaceutically acceptable pseudopolymorphic forms of compound of formula (X), preferably Form A, also referred to herein as the active pharmaceutical ingredients, may be administered by any route appropriate to the condition to be treated, preferably orally. It will be appreciated however, that the preferred route may vary with, for example, the condition of the recipient.

For each of the above-indicated utilities and indications the amount required of the active ingredient will depend upon a number of factors including the severity of the condition to be treated and the identity of the recipient and will ultimately be at the discretion of the attendant physician or veterinarian. The desired dose preferably may be presented as one, two, three or four or more subdoses administered at appropriate intervals throughout the day.

For an oral administration form, pseudopolymorphs of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the pseudopolymorphs of compound of formula (X), if desired with the substances customary therefor such as solubilizers, emulsifiers or further auxiliaries, are brought into solution, suspension, or emulsion. The pseudopolymorphs of compound of formula (X) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the pseudopolymorphs of compound of formula (X) in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

Pseudopolymorphs of the present invention may also be presented in a formulation comprising micrometer-, nanometer- or picometer-size particles of the pseudopolymorph of compound of formula (X), which formulation may contain other pharmaceutical agents and may optionally be converted to solid form.

It may be convenient to formulate the present pseudopolymorphs in the form of nanoparticles which have a surface modifier adsorbed on the surface thereof in an amount sufficient to maintain an effective average particle size of less than 1000 nm. Useful surface modifiers are believed to include those that physically adhere to the surface of the antiretroviral agent but do not chemically bind to the antiretroviral agent.

It may be further convenient to store the pseudopolymorphs of compound of formula (X) in packaging materials which are protective to mechanical, environmental, biological or chemical hazards, or degradation. Conditioning drug substances can be achieved by employing packaging materials impermeable to moisture, such as sealed vapour lock bags. Conditioning drug products, such as tablets, capsules, can be achieved by employing for instance, aluminium blisters.

It should be understood that in addition to the ingredients particularly mentioned above, formulations of this invention includes other agents conventional in the art having regard to the type of formulation in question, for example those suitable for oral administration may include flavouring agents or taste masking agents.

The following examples are intended for illustration only and are not intended to limit the scope of the invention in any way.

EXAMPLE 1

The industrial scale synthesis of Form A (1:1) was performed using the following steps. First a solution was prepared with isopropanol and (3R,3aS,6aR)-hexahydrofuro[2,3-b] furan-3-yl (1S,2R)-3-[[(4-aminophenyl) sulfonyl] (isobutyl) amino]-1-benzyl-2-hydroxypropylcarbamate. The solution was concentrated by vacuum distillation at 70° C. and 200-500 mbar pressure and cooled from a T>35° to a T between 15° and 20° C. for about 10 hours. The crystals formed were newly washed with 13 liters isopropanol and filtered. A subsequent recrystallization from ethanol/water (90 liters/90 liters) was performed. This was followed by a new dissolution step, but with 60 liters ethanol instead. Recrystallization of the reaction mixture from ethanol occurred, followed by a cooling step from reflux to −15° C. approximately and during 10 hours. The ethanolate formed was filtered and let to dry at about 50° C. and about 7 mbar. The yield of this process was at least 75%.

EXAMPLE 2

In another example a mixture of Form D and Form B were prepared. Acetone was used as a solvent during the crystallisation process to form Form D. The crystallisation process then comprised the step of stirring the initial starting compound (10 g) in 70 ml acetone. The solution was subsequently refluxed until the compound was completely solved. 40 ml of water were added and the solution was subsequently cooled slowly until room temperature and stirred overnight. Formed crystals were filtered and dried in the vacuum oven at 50° C. 7.6 g of product resulted from the crystallization, being the yield of this process of about 75%.

EXAMPLE 3

In another example Form J crystals were prepared. Isopropanol was used as a solvent during the crystallisation process to form Form J. The crystallisation process then comprised the step of solving the initial starting material in the hot solvent. The solution was subsequently cooled until room temperature. Formed crystals were filtered and dried in the vacuum oven at 50° C. The crystals contained about 50 mol % isopropanol.

EXAMPLE 4

In this example, the mass losses for different pseudopolymorphs in thermogravimetric (TG) experiments were calculated. Thermogravimetry is a technique that measures the change in mass of a sample as it is heated, cooled or held at constant temperature. Approximately 2 to 5 mg of sample were placed on a pan and inserted into the TG furnace, model Netzsch Thermo-Microbalance TG 209 coupled to a Bruker FTIR Spectrometer vector 22. The samples were heated in a nitrogen atmosphere at a rate of 10° C./min, up to a final temperature of 250° C. The detection limit of residual solvents was in the order of 0.1% for distinct stepwise solvent loss over a narrow temperature range (few degrees Celsius).

The following TG data were obtained:

Form A: a weight loss of 4.2% was observed in the temperature range of 25-138° C. (ethanol+little water) and of 6.9% (ethanol+$CO_2$) in the temperature range of 25-200° C. Ethanol loss rate was maximal at 120° C. $CO_2$ loss was due to chemical degradation and was visible at around 190° C.

Form B: a weight loss of 3.4% was observed in the temperature range 25-78° C. (water) and of 5.1% in the temperature range 25-110° C. (ethanol+water for T>78° C.). From 110-200° C. further 1.1% weight was lost (ethanol).

Form C: a weight loss of 2.1% was observed in the temperature range 25-83° C. (water+methanol) and of 4.2% in the temperature range 25-105° C. (methanol for T>83° C., distinct step). From 105-200° C. further 2.1% weight was lost (methanol). No ethanol was observed in the gas phase.

Form D: a weight loss of 0.1% was observed in the temperature range 25-50° C., of 4.2% in the temperature range 25-108° C. (acetone+ethanol for T>50° C.), of 8.2% in the temperature range 25-157° C. (acetone+ethanol for T>108° C.) and of 10.5% in the temperature range 25-240° C. (acetone+ethanol for T>157° C.).

Form E: a weight loss of 0.2% was observed in the temperature range 25-75° C. (water), of 1.8% in the temperature range 25-108° C. (dichloromethane+ethanol for T>75° C.), of 6.8% in the temperature range 25-157° C. (dichloromethane+ethanol for T>108° C.) and of 8.8% in the temperature range 25-240° C. (dichloromethane+ethanol for T>157° C.).

Form F: a weight loss of 0.1% was observed in the temperature range 25-50° C. (probably water), of 1.7% in the temperature range 25-108° C. (ethylacetate+ethanol for T>50° C.), of 6.6% in the temperature range 25-157° C. (ethylacetate+ethanol for T>108° C.) and of 9% in the temperature range 25-240° C. (ethylacetate+ethanol for T>157° C.).

Form G: a weight loss of 0.0% was observed in the temperature range 25-50° C., of 3.7% in the temperature range 25-108° C. (1-methoxy-2-propanol+ethanol for T>50° C., distinct step), of 8% in the temperature range 25-157° C. (1-methoxy-2-propanol+ethanol for T>108° C.) and of 12.5% in the temperature range 25-240° C. (1-methoxy-2-propanol+ethanol for T>157° C.).

Form H: a weight loss of 0.8% was observed in the temperature range 25-100° C. (anisole+little ethanol) and of 8.8% in the temperature range 25-200° C. (anisole ethanol for T>100° C.).

Form I: a weight loss of 0.3% was observed in the temperature range 25-89° C. (water) and of 11.0% in the temperature range 25-200° C. (tetrahydrofurane for T>89° C.). No ethanol was observed in the gas phase.

Table 10 shows approximate expected mass losses for different Forms in thermogravimetric (TG) experiments.

Mass loss in % ($M+x.LM=100\%$)

| Pseudo-polymorph | BP [°] | Hemisolvate | Monosolvate | Disolvate | Trisolvate |
|---|---|---|---|---|---|
| Form D | 56 | 5.0 | 9.6 | 17.5 | 24.1 |
| Form H | 152 | 9.0 | 16.5 | 28.3 | 37.2 |
| Form E | 40 | 7.2 | 13.4 | 23.7 | 31.8 |
| Form G | 119 | 7.6 | 14.1 | 24.8 | 33.1 |
| Form F | 76 | 7.4 | 13.9 | 24.3 | 32.6 |
| Form A | 78 | 4.0 | 7.8 | 14.4 | 20.2 |
| Form B | 100 | 1.6 | 3.2 | 6.2 | 9.0 |
| Form C | 65 | 2.8 | 5.5 | 10.5 | 14.9 |
| Form I | 66 | 6.2 | 11.6 | 20.8 | 28.3 |

In another set of thermogravimetric methods, Form A, Form A after Adsorption/Desorption, and Form A after Adsorption/Desorption hydratation tests, were all transferred into an aluminum sample pan. The TG curve was recorded on a TA Instrument Hi-Res TGA 2950 thermogravimeter at the following conditions:

initial temperature: room temperature
heating rate: 20° C./min
resolution factor: 4
final condition: 300° C. or <80 [(w/w) %]

Figure 16:
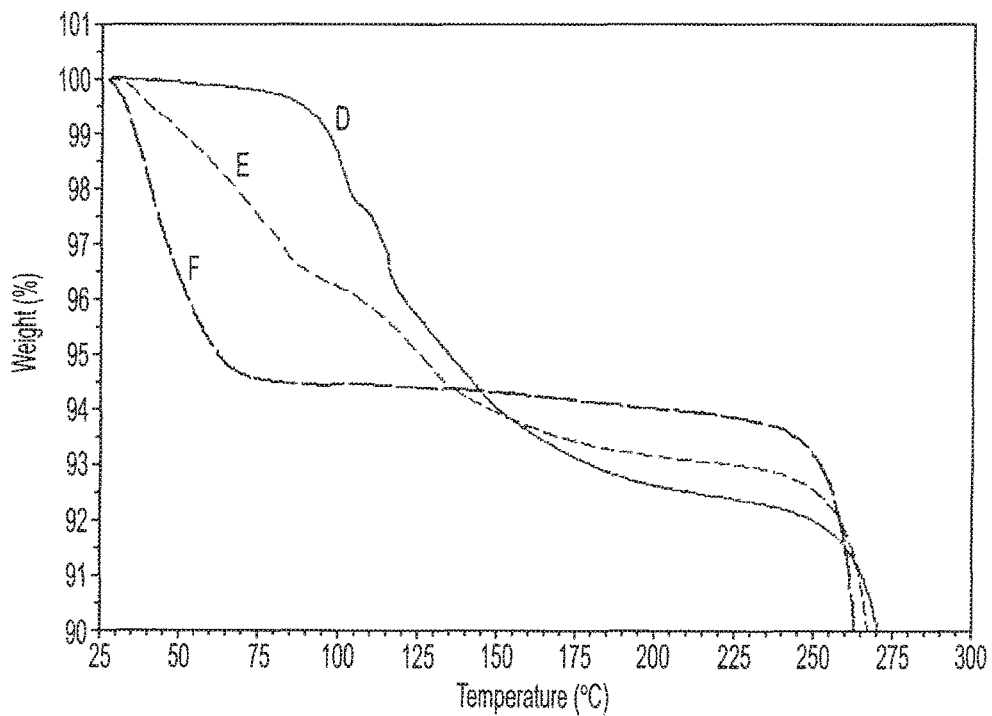
FIG. 16: Thermogravimetric (TG) curves of Form A (curve D), Form A after ADS/DES (curve E), and Form A after ADS/DES hydratation tests (curve F)

The TG curves of the samples are collected in FIG. 16. Table 11 shows mass losses for the forms tested:

| | TG (% weight change) | |
|---|---|---|
| Form A | Up to 80° C. | >80° C. |
| Form A | 0.3 | 7.1 |
| Form A after ADS/DES | 2.9 | 4.0 |
| Form A after A/D hydratation test | 5.4 | 0.5 |

Figure 17:
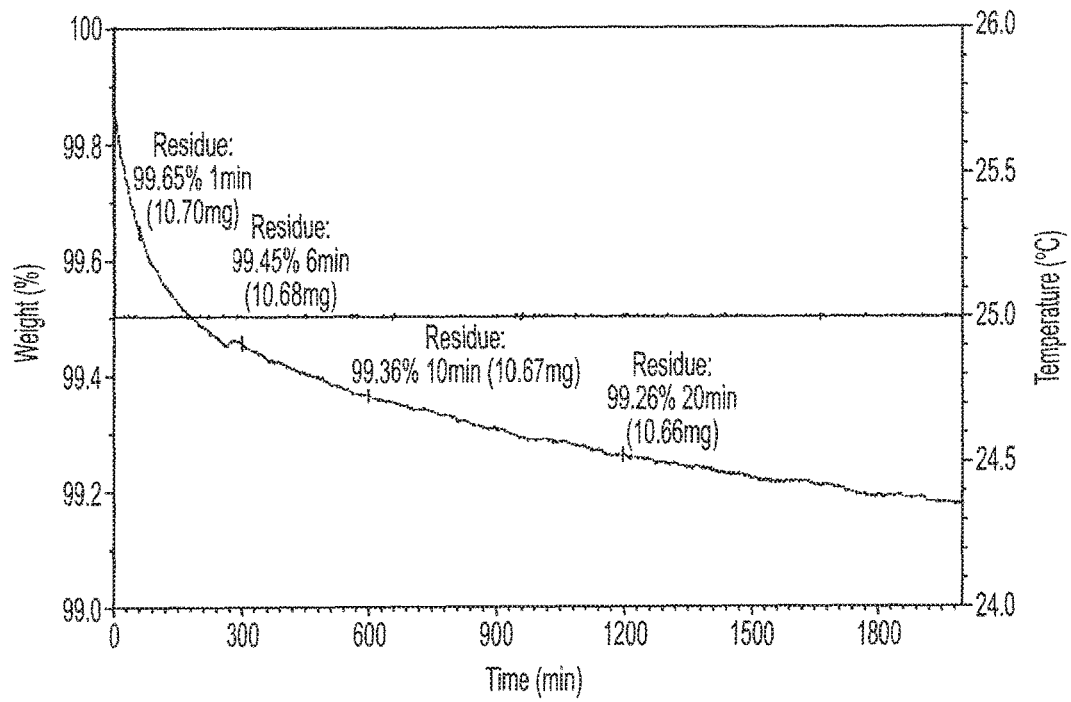
FIG. 17: TG curve of Form A at 25° C. under dry nitrogen atmosphere in function of time

The loss of weight at temperatures up to 80° C. is mainly due to the evaporation of solvent (water) present in the sample. The loss of weight at temperatures above 80° C. is mainly due to the evaporation of solvent (ethanolate) present in the sample, A TG curve of form A at 25° C. under dry nitrogen atmosphere in function of time is collected in FIG. 17. The loss of weight at 25° C. after 10 hours was around 0.6%. This was due to the evaporation of solvent.

EXAMPLE 5

In another example, measurements of differential scanning calorimetry (DSC) were also performed. For such purpose, a Perkin Elmer DSC 204 thermal analysis system was used. From 2 to 5 mg sample of Form A were accurately weighed into a DSC pan.

Figure 8:
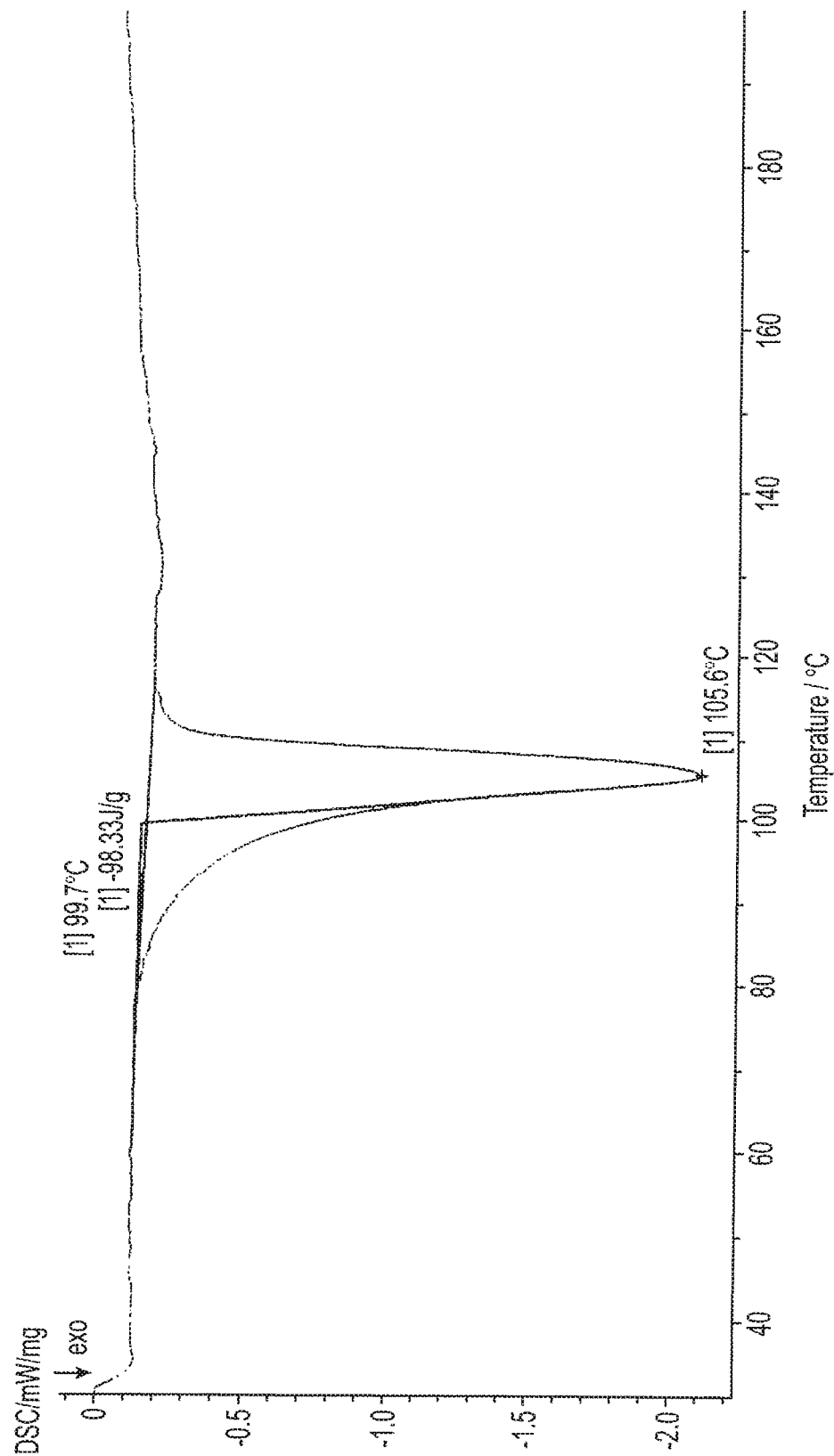
FIG. 8 is the Differential Scanning Calorimetric (DSC) thermograph of Form A (1:1).

The experiments were performed in an open pan. The sample was equilibrated to approximately 30° C. and then heated at a rate of 10° C. per minute, up to a final temperature of 200° C. The DSC data was obtained following a standard method in the art. The Form A was characterized by differential scanning calorimetry (DSC) in which it showed a sharp endotherm in the range 80-119° C., showing a peak at about 105.6° C., with a delta H=−98.33 J/g onset. Accordingly, the ethanol solvate crystal Form A of compound of formula (X) (1:1) showed the thermograph pattern, which appears in FIG. 8.

Figure 15:
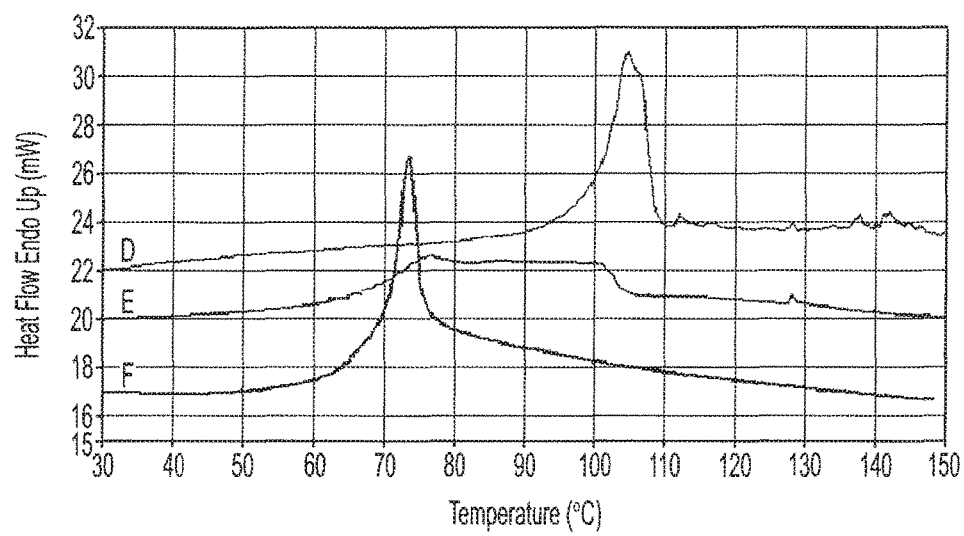
FIG. 15: DSC Thermograph curves of Form A (curve D), Form A after Adsorption/Desorption (ADS/DES) (curve E), and Form A after ADS/DES hydratation tests (curve F)

In another set of DSC measurements, Form A, Form A after Adsorption/Desorption, and Form A after Adsorption/Desorption hydratation tests were examined. About 3 mg of the samples were transferred into a 30 µl perforated aluminum Perkin Elmer sample pan. The sample pan was closed with the appropriate cover and the DSC curve recorded on a Perkin Elmer Pyris DSC, at the following conditions:
initial temperature: 25° C.
heating rate: 10° C./min
final temperature: 150° C.
nitrogen flow: 30 ml/min Form A showed an endothermic signal at about 104.6° C. and a heat of fusion of 95.8 J/g caused by the evaporation of the ethanolate and the melting of the product. Form A after ADS/DES showed a broad endothermic signal due to a mixture of ethanolate Form A and hydrated Form B. Form A after ADS/DES hydratation test showed an endothermic signal at about 73.5° C. and a heat of fusion of 126 J/g caused by the evaporation of water and the melting of the product. Thermograph curves are depicted in FIG. 15.

EXAMPLE 6

In another example stability studies of the Form A in three different conditions were tested out. They included conditions of 25° C. and 60% RH, 40° C. and 75% RH, and 50° C. These studies revealed that at 25° C. and 60% RH long-term stability, the amount of ethanol and water is stable.

Table 12 shows the Stability study for Form A. Long term stability at 25° C./60% RH (Relative Humidity), with brown glass bottles as sample container.

| Test | Release data | 0 month | 1 month | 3 month |
|---|---|---|---|---|
| Residual solvent: % (w/w) ethanol | 7.5 | 7.6 | 7.6 | 7.1 |
| % (w/w) Water | 0.10 | 0.27 | 0.26 | 0.55 |

EXAMPLE 7

Adsorption-Desorption Tests

About 23 mg of Form A were transferred into a VTI vapor sorption analyzer model SGA100 and the weight change with respect to the atmospheric humidity was recorded at the following conditions:

drying temperature: 40° C.
equilibrium: ≤0.05% in 5 min. or 60 min.
data interval: 0.05% or 2 min.
temperature: 25° C.
first cycle RH (%) adsorption: 5, 10, 20, 30, 40, 50, 60, 70, 80, 90, 95
  RH (%) desorption: 95, 90, 80, 70, 60, 50, 40, 30, 20, 10, 5
second cycle RH (%) adsorption: 5, 10, 20, 30, 40, 50, 60, 70, 80, 90, 95
  RH (%) desorption: 95, 90, 80, 70, 60, 50, 40, 30, 20, 10, 5

At the drying step about 0.6% weight loss was registered. The obtained dried product was not hygroscopic, it adsorbed up to 0.7% water at high relative humidity. During the desorption cycle a loss of weight of 1.4% was registered, this indicated that the product was losing ethanolate. The obtained product after ADS/DES was a mixture of ethanolate form and hydrated form.

Figure 18:
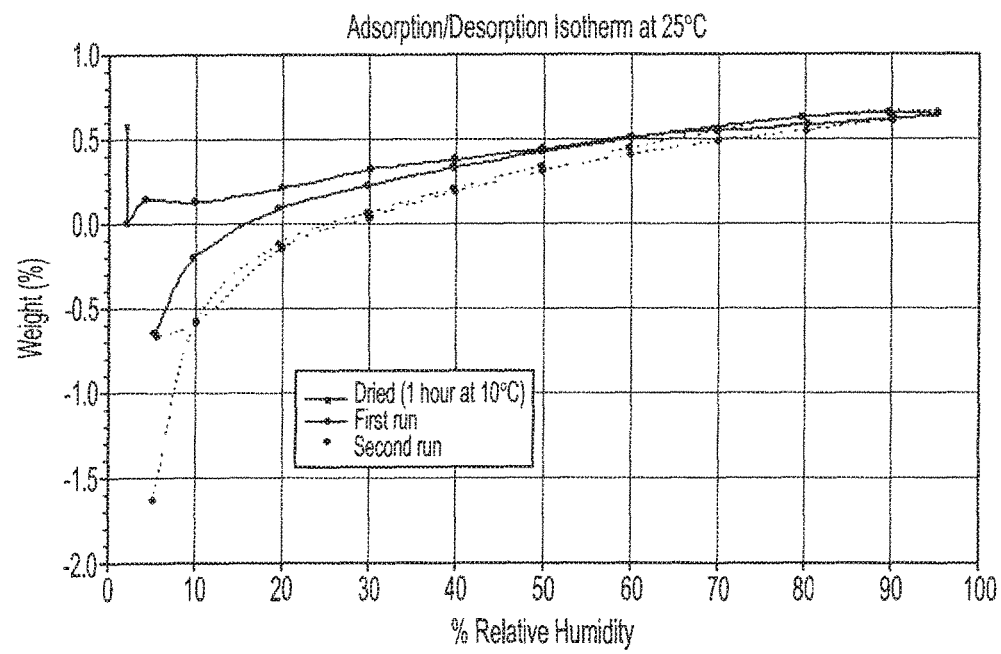
FIG. 18: ADS/DES curves of Form A.

The ADS/DES curve is collected in FIG. 18.

Adsorption-Desorption Hydratation Tests

Figure 19:
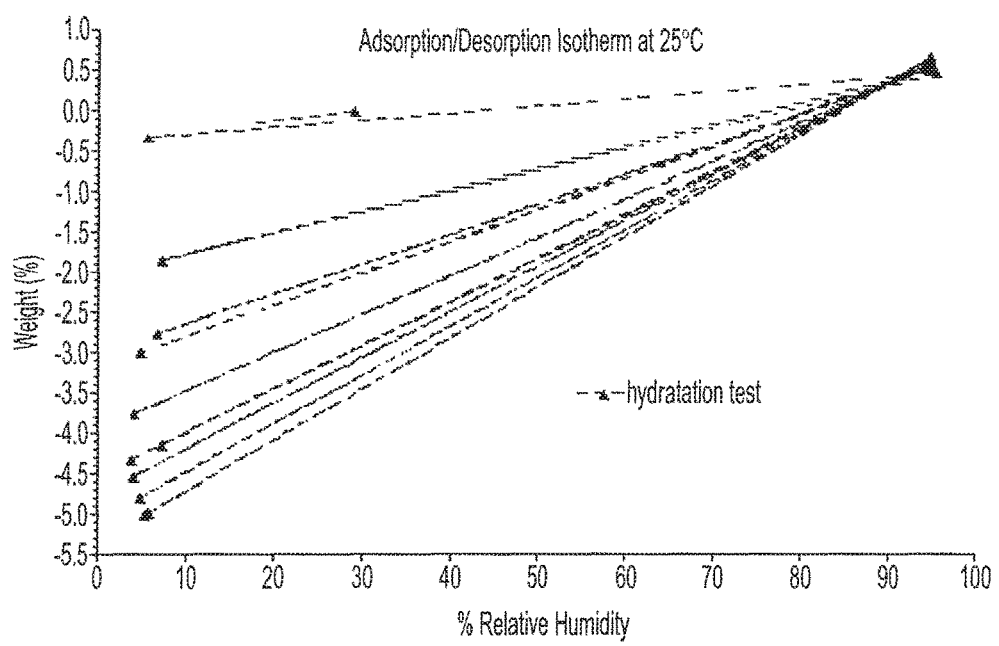
FIG. 19: ADS/DES curves of the hydratation test of Form A

About 23 mg of Form A were transferred into a VTI vapor sorption analyzer model SGA100 and the weight change with respect to the atmospheric humidity was recorded at the following conditions:
equilibrium: ≤0.0005% in 5 min. or 90 min.
data interval: 0.05% or 2 min
temperature: 25° C.
cycle RH (%) adsorption/desorption: 5.95
  repeat the cycle 11 times At the end of this test a loss of weight of 5.2% was registered. This was comparable with the TG result (TG 5.4% up to 80° C.). The ethanolate form was transferred into a hydrated form. The ADS/DES hydratation test curves are collected in FIG. 19.

EXAMPLE 8

The stability of Form A was studied after storage of the compound in a sample container with an inner cover made of single LD-PE (string sealed), and and outer cover made of PETP/Alu/PE (Moplast) heat sealed. A long term stability study at 25° C./60% RH, and an accelerated stability study at 40° C./75% RH, were performed for a period of 6 months, and the samples analysed at different time points as shown in following tables.

TABLE 13

| | | Long term stability at 25° C./60% RH | | | | | |
|---|---|---|---|---|---|---|---|
| tests | Remark | Specification | Release data | 0 month | 1 month | 3 month | 6 month |
| Polymorphism DSC | ° C. (onset) | For information only | 97.3 | 97.3 | 95.5 | 97.9 | 97.5 |
| | ° C. max | For information only | 104 | 104.2 | 103.5 | 104.2 | 104 |
| Residual solvents | % (w/w) ethanol | <=10.0% | 6.71 | 6.31 | 6.33 | 6.40 | 6.33 |
| | % (w/w) 2-propanol | <=0.5% | 0.04 | 0.04 | 0.05 | 0.05 | 0.05 |
| | % (w/w) THF | <=0.5% | <0.01 | <0.01 | <0.01 | <0.01 | <0.01 |
| | % (w/w) acetone | <=0.5% | <0.01 | <0.01 | <0.01 | <0.01 | <0.01 |
| | % (w/w) $CH_2Cl_2$ | <=0.06% | <0.01 | <0.01 | <0.01 | <0.01 | <0.01 |
| Water (KF) | % (w/w) | <=7.0% | 0.63 | 0.23 | 0.34 | 0.32 | 0.46 |
| X-Ray powder diffraction | | For information only | C | C | — | — | — |

C: chrystal

TABLE 14

Accelerated stability at 40° C./75% RH

| Tests | Remark | Specification | Release data | 0 month | 1 month | 3 month | 6 month |
|---|---|---|---|---|---|---|---|
| Polymorphism DSC | ° C. (onset) | For information only | 97.3 | 97.3 | 97.5 | 98.0 | 97.8 |
| | ° C. max | For information only | 104 | 104.2 | 103.4 | 1039 | 104.3 |
| Residual solvents | % (w/w) ethanol | <=10.0% | 6.71 | 6.31 | 6.73 | 6.32 | 6.50 |
| | % (w/w) 2-propanol | <=0.5% | 0.04 | 0.04 | 0.05 | 0.05 | 0.05 |
| | % (w/w) THF | <=0.5% | <0.01 | <0.01 | <0.01 | <0.01 | <0.01 |
| | % (w/w) acetone | <=0.5% | <0.01 | <0.01 | <0.01 | <0.01 | <0.01 |
| | % (w/w) CH$_2$Cl$_2$ | <=0.06% | <0.01 | <0.01 | <0.01 | <0.01 | <0.01 |
| Water (KF) | % (w/w) | <=7.0% | 0.63 | 0.23 | 0.37 | 0.34 | 0.42 |
| X-Ray powder diffraction | | For information only | C | C | — | — | — |

Form A exhibited chemical and crystallographic stability at the conditions mentioned in tables 13 and 14.

EXAMPLE 9

The stability of Form A was studied after storage of the compound in a sample container with an inner cover made of single LD-PE (string sealed), and and outer cover made of vapor loc bag (LPS) heat sealed. A long term stability study at 25° C./60% RH, and an accelerated stability study at 40° C./75% RH, were performed for a period of 6 months, and the samples analysed at different time points as shown in following tables.

Form A exhibited chemical and crystallographic stability at the conditions mentioned in tables 15 and 16.

EXAMPLE 10

For the purpose of chemical stability testing, Form A was stored for a period of 1, 4 and 8 weeks under different conditions. These conditions were 40° C./75% RH, 50° C., RT/<5% RH, RT/56% RH, RT/75% RH and 0.3 da ICH light. The compound was analysed after storage by HPLC and by visual inspection. The HPLC method used in this study was HPLC method 909. The results of the tests are reported in the following table.

TABLE 15

Long term stability at 25° C./60% RH

| Tests | Remark | Specification | Release data | 0 month | 1 month | 3 month | 6 month |
|---|---|---|---|---|---|---|---|
| Polymorphism DSC | ° C. (onset) | For information only | 97.3 | 97.3 | 96.3 | 96.2 | 98.5 |
| | ° C. max | For information only | 104 | 104.2 | 103.1 | 103.8 | 103.9 |
| Residual solvents | % (w/w) ethanol | <=10.0% | 6.71 | 6.31 | 6.42 | 6.35 | 6.52 |
| | % (w/w) 2-propanol | <=0.5% | 0.04 | 0.04 | 0.06 | 0.05 | 0.05 |
| | % (w/w) THF | <=0.5% | <0.01 | <0.01 | <0.01 | <0.01 | <0.01 |
| | % (w/w) acetone | <=0.5% | <0.01 | <0.01 | <0.01 | <0.01 | <0.01 |
| | % (w/w) CH$_2$Cl$_2$ | <=0.06% | <0.01 | <0.01 | <0.01 | <0.01 | <0.01 |
| Water (KF) | % (w/w) | <=7.0% | 0.63 | 0.23 | 0.32 | 0.38 | 0.49 |
| X-Ray powder diffraction | | For information only | C | C | — | — | — |

TABLE 16

Accelerated stability at 40° C./75% RH

| Tests | Remark | Specification | Release data | 0 month | 1 month | 3 month | 6 month |
|---|---|---|---|---|---|---|---|
| Polymorphism DSC | ° C. (onset) | For information only | 97.3 | 97.3 | 97.8 | 97.5 | 97.9 |
| | ° C. max | For information only | 104 | 104.2 | 103.4 | 103.7 | 104.0 |
| Residual solvents | % (w/w) ethanol | <=10.0% | 6.71 | 6.31 | 6.35 | 6.31 | 6.30 |
| | % (w/w) 2-propanol | <=0.5% | 0.04 | 0.04 | 0.06 | 0.05 | 0.05 |
| | % (w/w) THF | <=0.5% | <0.01 | <0.01 | <0.01 | <0.01 | <0.01 |
| | % (w/w) acetone | <=0.5% | <0.01 | <0.01 | <0.01 | <0.01 | <0.01 |
| | % (w/w) CH$_2$Cl$_2$ | <=0.06% | <0.01 | <0.01 | <0.01 | <0.01 | <0.01 |
| Water (KF) | % (w/w) | <=7.0% | 0.63 | 0.23 | 0.31 | 0.36 | 0.51 |
| X-Ray powder diffraction | | For information only | C | C | — | — | — |

TABLE 17

| Conditions | HPLC Sum of impurities | | | Appearance | | |
|---|---|---|---|---|---|---|
| | 1 week | 4 week | 8 week | 1 week | 4 weeks | 8 weeks |
| Reference | 1.07 | — | — | slightly-yellow | — | — |
| 0.3 da ICH light | 1.01 | — | — | slightly-yellow | — | — |
| 40° C./75% RH | 1.03 | 0.98 | 0.99 | slightly-yellow | slightly-yellow | slightly-yellow |
| 50° C. | 1.05 | 1.08 | 1.06 | slightly-yellow | slightly-yellow | slightly-yellow |
| RT/<5% RH | — | 1.02 | 1.04 | — | slightly-yellow | slightly-yellow |
| RT/56% RH | — | 1.02 | 0.99 | — | slightly-yellow | slightly-yellow |
| RT/75% RH | — | 1.00 | 1.01 | — | slightly-yellow | slightly-yellow |

It was concluded that Form A is chemically stable after storage in all investigated conditions.

EXAMPLE 11

Different fractions of Form B were characterized with thermogravimetry (TG), differential scanning calorimetry (DSC) and infrared spectroscopy (IR). The results of the tests are reported in the following table.

TABLE 18

| Fractions | TG % weight change <100° C. | IR | DSC Max (° C.) | Extra (° C.) |
|---|---|---|---|---|
| Form B fraction 1 | 5.65 | Hydrate, Ref | 69.1 | — |
| after ADS/DES | 4.30 | ±Hydrate, Ref, +amorphous | — | — |
| Form B fraction 2 | 5.91 | ~Hydrate, Ref | 75.6 | — |
| after 5 d 40° C./75% RH | 3.56 | ~Hydrate, Ref | 74.1 | — |
| Form B fraction 3 | 3.13 | ±Hydrate, Ref, +amorphous | 77.0 | 67.8 |
| after 5 d 40° C./75% RH | 2.33 | ±Hydrate, Ref, +amorphous | 77.4 | 62.8 |

~hydrate, Ref: identical with reference

EXAMPLE 12

Figure 20:
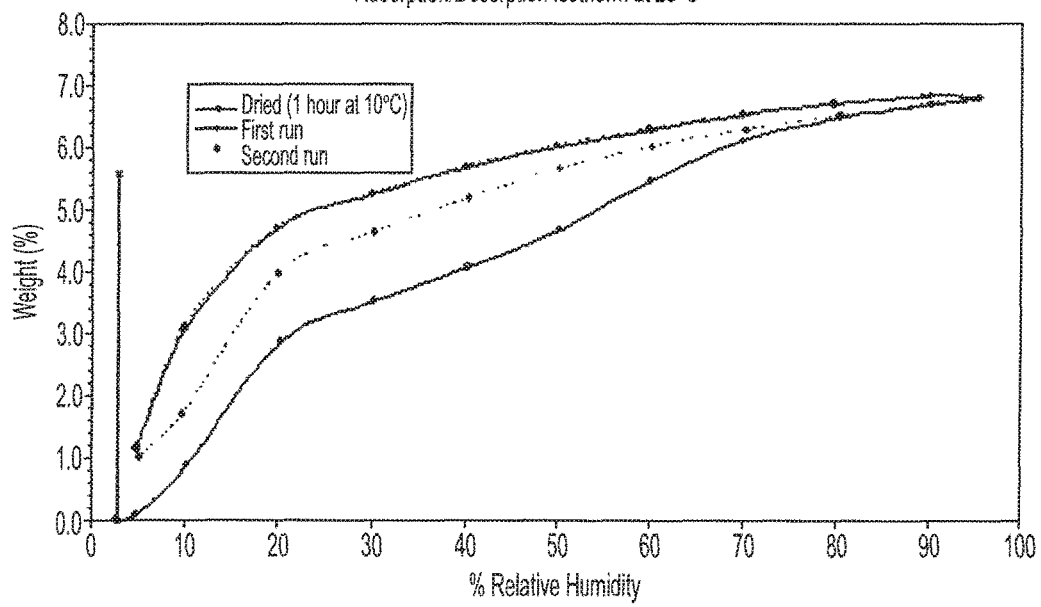
FIG. 20: ADS/DES curves of Form B

The adsorption and desorption of water at 25° C. at different conditions of relative humidity was investigated on 38 mg of Form B. The weight change as a function of relative humidity was registered. The results are displayed in FIG. 20. At the drying step about 5.6% weight loss was registered for Form B. The obtained dried product was hygroscopic, it adsorbed up to 6.8% water at high relative humidity. After the desorption cycle about 1.2% water remained on the sample. The obtained product after ADS/DES was a mixture of hydrate and amorphous product.

EXAMPLE 13

Aqueous solubilities of Form B were measured in solvents with different pH. An excess of the solute was equilibrated with the solvent at 20° C. for at least 24 hours. After removing the undissolved compound, the concentration in solution was determined using UV spectrometry.

TABLE 19

| Solvent | Solubility (mg/100 ml solution) |
|---|---|
| Water | 10 (pH 5.1) |
| Buffer pH 2 (citrate/HCl) | 23 (pH 2.0) |
| Buffer pH 3 (citrate/HCl) | 13 (pH 3.0) |
| Buffer pH 4 (citrate/HCl) | 12 (pH 4.0) |
| 0.01N HCl | 18 (pH 2.1) |
| 0.1N HCl | 150 (pH 1.1) |
| 1.0N HCl | 510 (pH 0.14) |

EXAMPLE 14

The stability of the crystal structure of Form B was studied after storage of the compound for a period of two weeks at room temperature (RT) under <5%, 56% and 75% relative humidity (RH), 50° C. and 40° C./75% RH. The samples were analyzed with thermogravimetry (TG), differential scanning calorimetry (DSC), infrared spectroscopy (IR) and X-ray diffraction (XRD). The results of the tests are reported in the following table.

TABLE 20

| condition | TG <100° C. | <225° C. | IR | XRD | DSC Max (° C.) | Appearance |
|---|---|---|---|---|---|---|
| 0 days | 5.65 | 0.16 | Ref | Ref | 69.1 | slightly yellow-orange |
| after ADS/DES | 4.30 | 0.18 | ≠Ref | — | — | slightly yellow-orange |
| RT/<5% RH | 0.32 | 0.07 | ≠Ref | ≠Ref | 71.2 | slightly yellow-orange |
| RT/56% RH | 5.71 | 0.25 | ~Ref | ~Ref | 71.0 | slightly yellow-orange |
| RT/75% RH | 6.20 | 0.10 | ~Ref | ~Ref | 71.5 | slightly yellow-orange |
| 50° C. | 0.23 | 0.06 | ≠Ref | ≠Ref | 76.4 | slightly yellow-orange |
| 40° C. 75% RH | 5.77 | 0.07 | ~Ref | ±Ref | 70.4 | slightly yellow-orange |

~Ref: identical with reference
±Ref: similar with reference
≠Ref: different with reference

EXAMPLE 15

In the chemical stability test program Form B was stored for a period of 1, 4 and 9 weeks under different conditions. These conditions were 40° C./75% RH, 50° C., RT/<5% RH, RT/56% RH, RT/75% RH and 0.3 da ICH light. The compound was analysed after storage by HPLC and by visual inspection. The HPLC method used in this study was HPLC method 909. The results of the tests are reported in the following table, from which it was concluded that Form B is chemically stable.

TABLE 21

| Condition | HPLC Sum of impurities | | | Appearance | | |
|---|---|---|---|---|---|---|
| | 1 week | 4 week | 9 week | 1 week | 4 weeks | 9 weeks |
| Reference | 1.35 | — | — | lightly yellow-orange | — | — |
| 0.3 da ICH light | 1.30 | — | — | light-orange | — | — |
| 40° C./75% RH | 1.43 | 1.38 | 1.41 | lightly yellow-orange | Orange | light-orange |
| 50° C. | 1.46 | 1.50 | 1.46 | lightly yellow-orange | light-orange | light-orange |
| RT/<50% RH | — | 1.48 | 1.37 | — | light-orange | light-orange |
| RT/56% RH | — | 1.11 | 1.35 | — | lightly yellow-orange | light-orange |
| RT/75% RH | — | 1.34 | 1.29 | — | light-orange | light-orange |

EXAMPLE 16

Form K was prepared by adding neat methanesulfonic acid to a solution of Form A in THF at r.t. Form K was subsequently mixed with alkali halide and pressed to a pellet (Ph. Eur.) and analyzed by Infrared spectrometry (IR) at the following conditions:
 apparatus: Nicolet Magna 560 FTIR spectrophotometer
 number of scans: 32
 resolution: 1 cm$^{-1}$
 wavelength range: 4000 to 400 cm$^{-1}$
 baseline correction: yes
 detector: DTGS with KBr windows
 beamsplitter: Ge on KBr
 alkali halide: KBr (potassium bromide)

Figure 21:
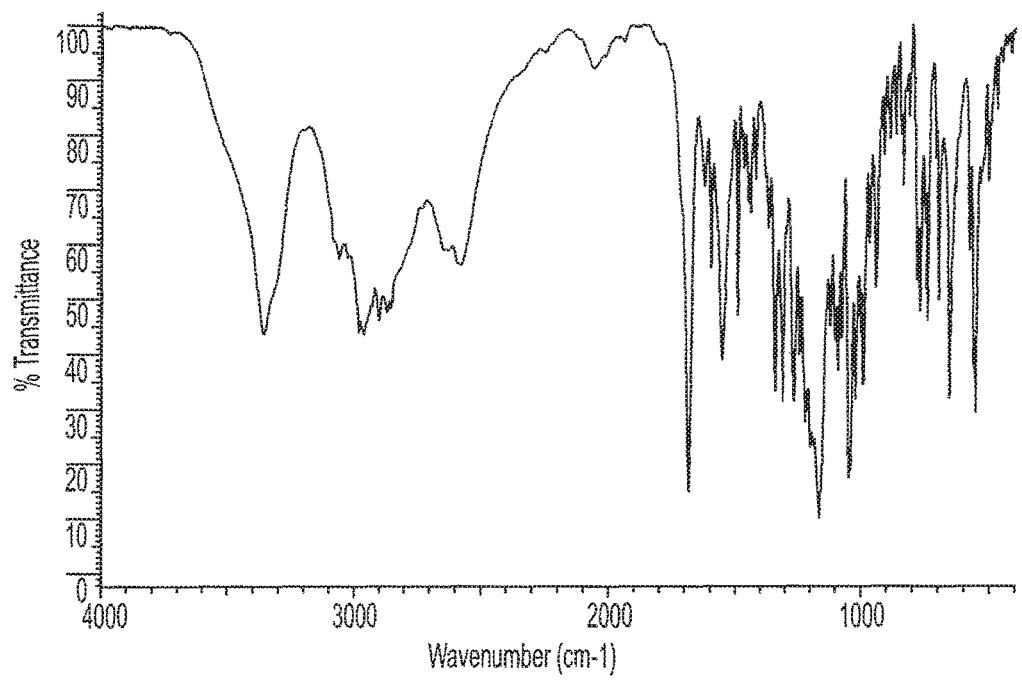
FIG. 21: IR spectrum of Form K

The IR spectrum of Form K, as shown in FIG. 21, reflects the vibrational modes of the molecular structure of the mesylate solvate as a crystalline product.

TABLE 22

Wavenumbers (cm$^{-1}$) and relative intensities of absorption bands($^1$)

3362m, 3064w
2985m, 2964m, 2906m, 2873m, 2632w, 2585w
1687s, 1627w, 1601w
1554m, 1495m, 1480w, 1470w, 1452w, 1443w, 1421w
1383w, 1373w, 1369w, 1345m, 1324m, 1314m, 1299w, 1268m,
1245m, 1221m, 1202s
1190s, 1166vs, 1122m, 1091m, 1077m, 1051s, 1043s, 1023m, 1002m
992m, 969w, 943w, 912w, 888w, 867vw, 836w, 813vw
773m, 754w, 743m, 711w, 700m, 658m, 634w
581w, 556m, 505w, 472vw, 452vw, 435vw, 417vw ($^1$)vs = very strong, s = strong, m = medium, w = weak, vw = very weak, br = broad

EXAMPLE 17

Figure 22:
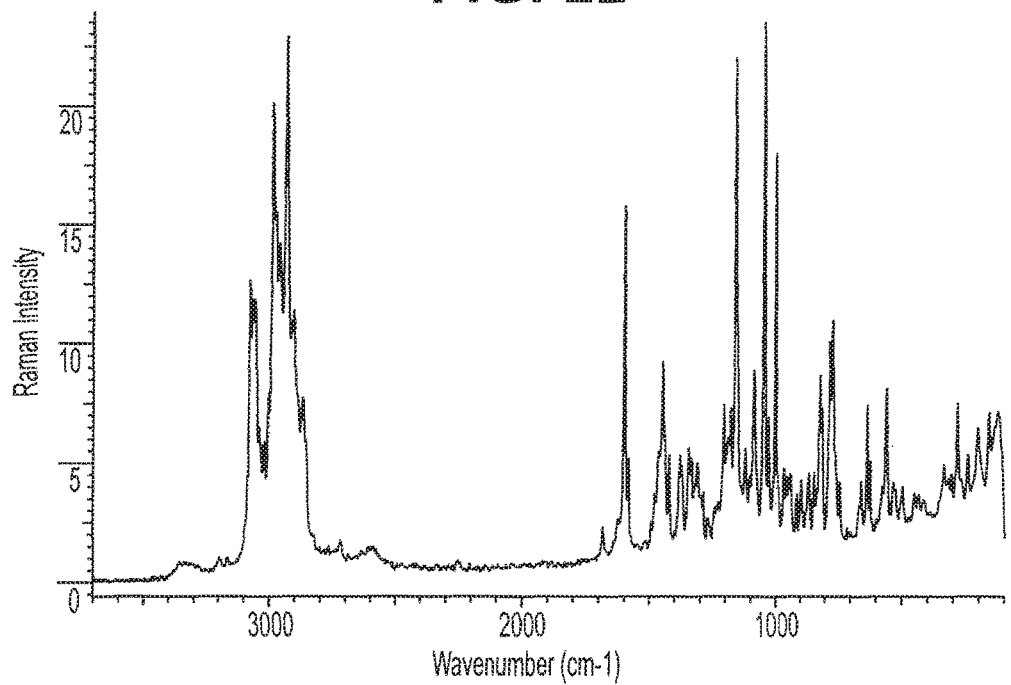
FIG. 22: Raman spectrum of Form K

Form K was transferred to a glass capillary cell and analyzed by Raman spectrometry at the following conditions:
 Raman mode: Nondispersive Raman
 apparatus: Nicolet FT-Raman module
 number of scans: 64
 resolution: 4 cm$^{-1}$
 wavelength range: 3700 to 100 cm$^{-1}$
 laser: Nd:YVO4
 laser frequency: 1064 cm$^{-1}$
 detector: InGaAs
 beamsplitter: CaF$_2$
 sample geometry: 180° reflective
 polarization: no The Raman spectrum of Form K, as shown in FIG. 22, reflects the vibrational modes of the molecular structure of the mesylate as a crystalline product.

TABLE 23

Wavenumbers (cm$^{-1}$) and relative intensities of absorption bands($^1$)

3080m, 3068m, 3059m, 3043w, 3022w, 3006m
2989s, 2978s, 2962s, 2933vs, 2906m, 2871m
1685vw, 1628w, 1603s, 1585w, 1495w, 1479w, 1466w, 1450m, 1423w
1381w, 1346w, 1336w, 1313w, 1290w, 1271w, 1244w, 1230w, 1209m
1190w, 1182m, 1163vs, 1122w, 1105w, 1090m, 1049vs, 1032w, 1003s
968w, 955w, 941w, 914w, 897w, 877w, 866w, 845w, 823m, 814m
783m, 771m, 742w, 658w, 634m, 621w
577w, 561m, 534w, 524w, 497w, 451w, 436w
337w, 308w, 287m, 247w, 206w, 162m, 129m ($^1$)vs = very strong, s = strong, m = medium, w = weak, vw = very weak

EXAMPLE 18

Figure 23:
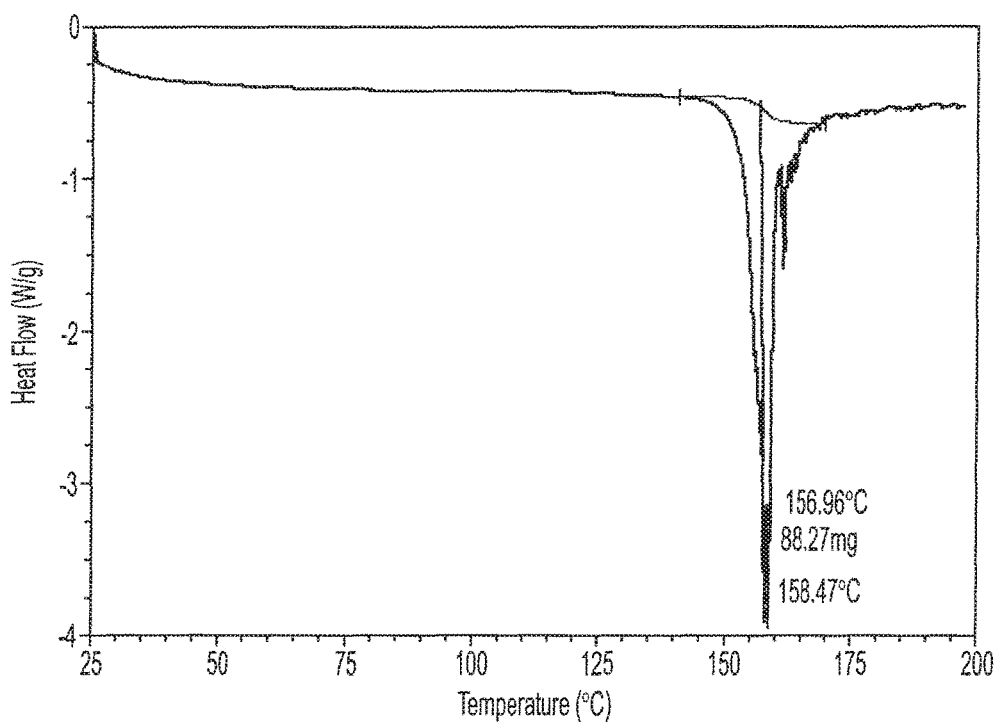
FIG. 23: DSC curve of Form K

About 3 mg of Form K were transferred into a standard aluminium TA-Instrument sample pan. The sample pan was closed with the appropriate cover and the DSC curve recorded on a TA-Instruments Q1000 MTDSC equipped with a RCS cooling unit, at the following conditions:
 initial temperature: 25° C.
 heating rate: 10° C./min
 final temperature: 200° C.
 nitrogen flow: 50 ml/min The DSC curve as depicted in FIG. 23, shows the melting with decomposition of a crystalline product. The melting of Form K occurs at 158.4° C. Due to the decomposition, the heat of fusion calculation can only be used to indicate the crystalline property of the product.

EXAMPLE 19

Form K was transferred into an aluminum sample pan. The TG curve was recorded on a TA Instruments Hi-Res TGA 2950 thermogravimeter at the following conditions:
 initial temperature: room temperature
 heating rate: 20° C./min
 resolution factor: 4
 final condition: 300° C. or <80 [(w/w) %]

Figure 24:
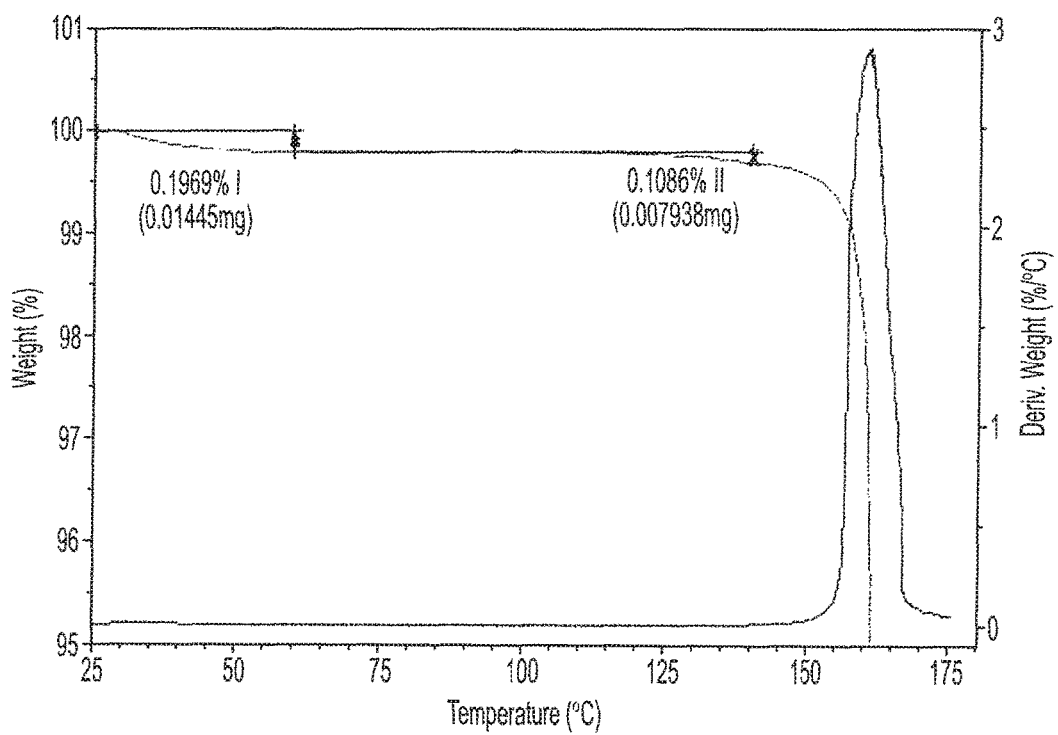
FIG. 24: TG curve of Form K

The TG curve is exhibited in FIG. 24. The loss of weight of around 0.2% up to 60° C. was due to the evaporation of solvent. The loss of weight at temperatures above 140° C. was due to the evaporation and decomposition of the product.

EXAMPLE 20

Adsorption-Desorption

About 21 mg of Form K were transferred into a VTI vapor sorption analyzer model SGA100 and the weight change with respect to the atmospheric humidity was recorded at the following conditions:

drying temperature: 40° C.
equilibrium: ≤0.05% in 5 min. or 60 min.
data interval: 0.05% or 2.0 min.
temperature: 25° C.
first cycle RH (%) adsorption: 5, 10, 20, 30, 40, 50, 60, 70, 80, 90, 95
  RH (%) desorption: 95, 90, 80, 70, 60, 50, 40, 30, 20, 10, 5
second cycle RH (%) adsorption: 5, 10, 20, 30, 40, 50, 60, 70, 80, 90, 95
  RH (%) desorption: 95, 90, 80, 70, 60, 50, 40, 30, 20, 10, 5

Figure 25:
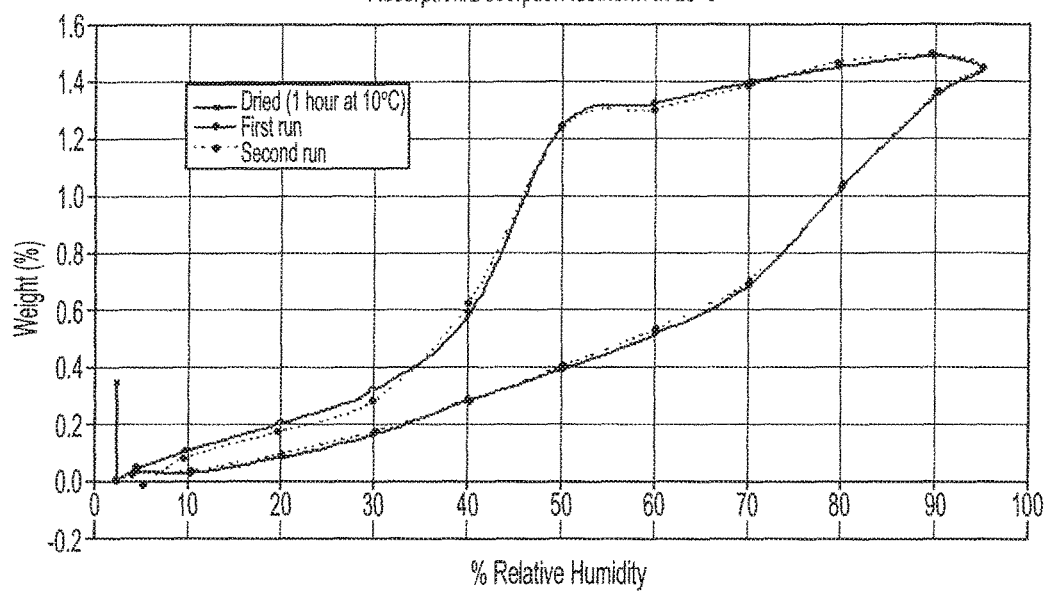
FIG. 25: ADS/DES isotherm of Form K, batch 1

The Adsorption-Desorption isotherm is shown in FIG. 25. Form K is hygroscopic. At the initial drying step a loss of weight of 0.3% was registered, comparable to the TG result. Form K adsorbed up to 1.5% water at high relative humidity. The product dried completely during the desorption cycle.

Figure 26:
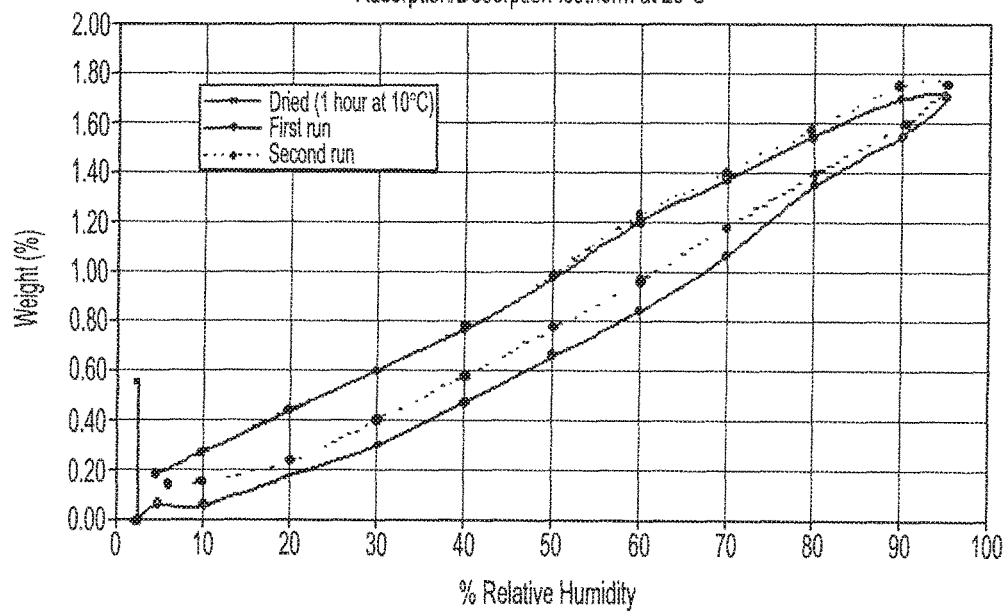
FIG. 26: ADS/DES isotherm of Form K, batch 2

A different study of the adsorption and desorption of water by Form K at 25° C. at different conditions of relative humidity was investigated on an amount of about 18 mg of the mesylate solvate. The weight change as a function of relative humidity was registered. The result is displayed in FIG. 26.

At the drying step about 0.6% weight loss is registered for Form K. The obtained dried product is slightly hygroscopic, it adsorbed up to 1.7% water at high relative humidity. The product dried completely during the desorption cycle.

EXAMPLE 21

Aqueous solubilities of Form K were measured in solvents with different pH. An excess of the solute was equilibrated with the solvent at 20° C. for at least 48 hours. After removing the undissolved compound, the concentration in solution was determined using UV spectrometry.

TABLE 24

| Solvent | Solubility (mg/100 ml solution) |
|---|---|
| Water | 19 (pH 3.3) |
| Buffer pH 2 (citrate/HCl) | 21 (pH 2.0) |
| Buffer pH 3 (citrate/HCl) | 12 (pH 3.0) |
| Buffer pH 4 (citrate/HCl) | 11 (pH 4.0) |
| 0.01N HCl | 24 (pH 2.0) |
| 20% HPβCD in water | 2100 (pH 1.6) |

EXAMPLE 22

The stability of the crystal structure of Form K batch 1 was studied after storage of the compound for a period of four weeks at room temperature (RT) under 75% relative humidity (RH), 50° C. and 40° C./75% RH. The stability of the crystal structure of Form K batch 2 was studied after storage of the compound for a period of four weeks at room temperature (RT) under <5%, 56% and 75% relative humidity (RH), 50° C. and 40° C./75% RH. The samples were analyzed with thermogravimetry (TG), differential scanning calorimetry (DSC) and infrared spectroscopy (IR). The results of the tests are reported in the following table.

TABLE 25

| | | TG | | | DSC | | |
|---|---|---|---|---|---|---|---|
| compound | conditions | <80° C. | <125° C. | IR | Max (° C.) | Extra (° C.) | Appearance |
| Form K | 0 days | 0.47 | 0.15 | Ref | 143.7 | — | slightly orange |
| Batch 1 | RT/75% RH | 2.87 | 0.19 | ≠Ref | 146.6 | 64.3 | slightly orange |
| | 50° C. | 0.32 | 0.14 | ~Ref | 140.6 | 45.6 | orange |
| | 40° C./75% RH | 1.48 | 3.71 | — | — | — | brown oil |
| Form K | 0 days | 0.16 | 0.11 | Ref | 155.8 | — | slightly orange |
| Batch 2 | RT/<5% RH | 0.00 | 0.03 | ~Ref | 156.9 | — | slightly orange |
| | RT/56% RH | 0.27 | 0.03 | ±Ref | 154.6 | — | slightly orange |
| | RT/75% RH | 1.82 | 0.07 | ≠Ref | 149.2 | 67.0 | slightly orange |
| | 50° C. | 0.12 | 0.12 | ~Ref | 156.8 | — | slightly orange |
| | 40° C./75% RH | 3.26 | 3.08 | — | — | — | brown oil |

~Ref: identical with reference
±Ref: similar with reference
≠Ref: different with reference

EXAMPLE 23

In the chemical stability test program Form K batch 1 was stored for a period of 1 and 4 weeks under different conditions. These conditions were 40° C./75% RH, 50° C., RT/75% RH and 0.3 da ICH light. Form K batch 2 was also stored for a period of 1 and 4 weeks under different conditions. These conditions were 40° C./75% RH, 50° C., RT/<5% RH, RT/56% RH, RT/75% RH and 0.3 da ICH light. The compound was analysed after storage by HPLC and by visual inspection. The HPLC method used in this study was HPLC method 909. The results of the tests are reported in the following table.

TABLE 26

| compound | conditions | HPLC Sum of impurities | | appearance | |
|---|---|---|---|---|---|
| | | 1 week | 4 weeks | 1 week | 4 weeks |
| Form K batch 1 | Reference | 3.57 | — | slightly-orange | — |
| | 0.3da ICH light | 2.93 | — | slightly-orange | — |
| | 40° C./75% RH | 5.36 | >90* | slightly-orange | brown oil |
| | 50° C. | 3.99 | 27.53 | slightly-orange | orange |
| | RT/75% RH | — | 3.61 | — | slightly-orange |
| Form K Batch 2 | Reference | 1.50 | — | slightly-orange | — |
| | 0.3da ICH light | 1.17 | — | slightly-orange | — |
| | 40° C./75% RH | 1.75 | >85* | slightly-orange | brown oil |
| | 50° C. | 1.46 | 1.25 | slightly-orange | slightly-orange |
| | RT/<5% RH | — | 1.58 | — | slightly-orange |
| | RT/56% RH | — | 1.45 | — | slightly-orange |
| | RT/75% RH | — | 1.46 | — | slightly-orange |

EXAMPLE 24

A randomized, placebo-controlled, double-blind, multiple dose escalation trial was performed to examine the safety, tolerability and pharmacokinetics of Form A after oral administration twice or three times daily, in healthy subjects. Four dosages of Form A (400 mg b.i.d., 800 mg b.i.d., 800 mg t.i.d., and 1200 mg t.i.d.) were tested in 4 panels of 9 healthy subjects. Within each panel, 6 subjects were treated with Form A and 3 subjects with placebo for 13 days with a single intake in the morning of day 14. (b.i.d.=twice daily, t.i.d.=three times daily).

Form A was readily absorbed and concentration-time profiles of Form A after repeated dosing were dependent on the dose administered. Steady-state plasma concentrations were reached generally within 3 days, although $C_{0\,h}$ (conc. at administration time) and $AUC_{24\,h}$ (area under de curve or bioavailability) slightly decreased over time at all dose levels. $AUC_{24\,h}$ and $C_{ss,av}$ (conc. at average steady-state) were dose-proportional (daily dose) at 400 mg b.i.d., 800 mg t.i.d. and 1200 mg t.i.d., but was more than dose-proportional at 800 mg b.i.d. $C_{max}$ (maximum conc.) was dose-proportional with respect to dose per intake. Less than 2% of unchanged Form A was excreted in the urine at all dose levels.

The invention claimed is:

1. A process for preparing a pseudopolymorph of the compound (3R,3aS,6aR)-hexahydrofuro [2,3-b] furan-3-yl (1 S,2R)-3-[[(4-aminophenyl) sulfonyl] (isobutyl) amino]-1-benzyl-2-hydroxypropylcarbamate comprising
combining (3R,3aS,6aR)-hexahydrofuro [2,3-b] furan-3-yl (1 S,2R)-3-[[(4-aminophenyl) sulfonyl] (isobutyl) amino]-1-benzyl-2-hydroxypropylcarbamate with an organic solvent, water, or a mixture of water and a water miscible organic solvent, and inducing crystallization.

2. The process of claim 1, wherein the pseudopolymorph is a hydrate solvate, alcohol solvate, alkane solvate, ketone solvate, ether solvate, cycloether solvate, ester solvate, or sulfonic solvate.

3. The process of claim 1, wherein the pseudopolymorph is a hydrate solvate, C1-C4 alcohol solvate, C1-C4 chloroalkane solvate, C1-C5 ketone solvate, C1-C4 ether solvate, cycloether solvate, C1-C5 ester solvate, or C1-C4 sulfonic solvate.

4. The process of claim 1, wherein the pseudopolymorph is Form A (ethanolate), Form B (hydrate), Form C (methanolate), Form D (acetonate), Form E (dichloromethanate), Form F (ethylacetate solvate), Form G (1-ethoxy-2-propanolate), Form H (anisolate), Form I (tetrahydrofuranate), Form J (isopropanolate), or Form K (mesylate).

5. The process of claim 1, wherein the pseudopolymorph is a hydrate solvate.

6. The process of claim 1, wherein the pseudopolymorph is a C1-C4 alcohol solvate.

7. The process of claim 1, wherein the pseudopolymorph is an ethanolate solvate.

8. The process of claim 1, wherein the pseudopolymorph is Form B (hydrate).

9. The process of claim 1, wherein the pseudopolymorph is Form A (ethanolate).

10. The process of claim 1, wherein the pseudopolymorph is prepared starting from the isopropanolate solvate of (3R,3aS,6aR)-hexahydrofuro [2,3-b] furan-3-yl (1 S,2R)-3-[[(4-aminophenyl) sulfonyl] (isobutyl) amino]-1-benzyl-2-hydroxypropylcarbamate.

11. The process of claim 1, comprising combining (3R,3aS,6aR)-hexahydrofuro [2,3-b] furan-3-yl (1 S,2R)-3-[[(4-aminophenyl) sulfonyl] (isobutyl) amino]-1-benzyl-2-hydroxypropylcarbamate with a C1-C4 alcohol, water, or a mixture of a C1-C4 alcohol and water.

12. The process of claim 5, wherein the ratio of compound to water in the pseudopolymorph ranges between 5:1 and 1:5.

13. The process of claim 5, wherein the ratio of compound to water in the pseudopolymorph ranges between about 0.2:1 and about 3:1.

14. The process of claim 5, wherein the ratio of compound to water in the pseudopolymorph ranges between about 1:1 and about 2:1.

15. The process of claim 5, wherein the ratio of compound to water in the pseudopolymorph is about 1:1.

16. The process of claim 6, wherein the ratio of compound to C1-C4 alcohol in the pseudopolymorph ranges between 5:1 and 1:5.

17. The process of claim 6, wherein the ratio of compound to C1-C4 alcohol in the pseudopolymorph ranges between about 0.2:1 and about 3:1.

18. The process of claim 6, wherein the ratio of compound to C1-C4 alcohol in the pseudopolymorph ranges between about 1:1 and about 2:1.

19. The process of claim 6, wherein the ratio of compound to C1-C4 alcohol in the pseudopolymorph is about 1:1.

* * * * *